US010150796B2

(12) United States Patent
Tarran et al.

(10) Patent No.: US 10,150,796 B2
(45) Date of Patent: *Dec. 11, 2018

(54) PEPTIDE INHIBITORS OF SODIUM CHANNELS

(71) Applicants: The University of North Carolina at Chapel Hill, Chapel Hill, NC (US); Spyryx Biosciences, Inc., Durham, NC (US)

(72) Inventors: Robert Tarran, Chapel Hill, NC (US); Dale J. Christensen, Cary, NC (US)

(73) Assignees: University of North Carolina at Chapel Hill, Chapel Hill, NC (US); Spyryx Biosciences, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/591,684

(22) Filed: May 10, 2017

(65) Prior Publication Data

US 2017/0327538 A1 Nov. 16, 2017

Related U.S. Application Data

(63) Continuation of application No. 14/878,720, filed on Oct. 8, 2015, now abandoned.

(60) Provisional application No. 62/061,461, filed on Oct. 8, 2014.

(51) Int. Cl.
| | |
|---|---|
| *C07K 7/08* | (2006.01) |
| *C07K 16/00* | (2006.01) |
| *C07K 7/06* | (2006.01) |
| *A61K 9/00* | (2006.01) |
| *C07K 5/062* | (2006.01) |
| *C07K 14/705* | (2006.01) |
| *A61K 38/00* | (2006.01) |

(52) U.S. Cl.
CPC .............. *C07K 7/08* (2013.01); *A61K 9/0073* (2013.01); *C07K 5/06026* (2013.01); *C07K 7/06* (2013.01); *C07K 14/705* (2013.01); *A61K 38/00* (2013.01); *C07K 2319/00* (2013.01); *C07K 2319/10* (2013.01)

(58) Field of Classification Search
None
See application file for complete search history.

(56) References Cited

U.S. PATENT DOCUMENTS

| 7,951,781 B2 | 5/2011 | McCray, Jr. et al. |
| 9,127,040 B2 | 9/2015 | Tarran et al. |
| 9,549,967 B2 | 1/2017 | Tarran et al. |
| 2005/0192221 A1 | 9/2005 | McCray, Jr. et al. |
| 2005/0244334 A1 | 11/2005 | Castillo et al. |
| 2008/0312093 A1 | 12/2008 | Inazawa et al. |
| 2009/0110756 A1 | 4/2009 | McCray, Jr. et al. |
| 2009/0197800 A1 | 8/2009 | Schaffer et al. |
| 2012/0115795 A1 | 5/2012 | Tarran et al. |
| 2016/0159879 A1 | 6/2016 | Tarran et al. |

FOREIGN PATENT DOCUMENTS

| WO | 2006/027052 A2 | 3/2006 |
| WO | 2009/074575 A2 | 6/2009 |
| WO | 2010/138794 A2 | 12/2010 |
| WO | 2012129077 A2 | 9/2012 |
| WO | 2013/043720 A1 | 3/2013 |
| WO | 2013043720 A1 | 3/2013 |

OTHER PUBLICATIONS

Zhou et al., The βENaC-overexpressing mouse as a model of cystic fibrosis lung disease, 2011, Journal of Cystic Fibrosis vol. 10 Suppl 2, pp. S172-S182.*
Brinckerhoff, et al., "Terminal Modifications Inhibit Proteolytic Degradation of an Immunogenic MART-1 27-35 Peptide: Implications for Peptide Vaccines", Int. J. Cancer v, 83, (1999), pp. 326-334.
The International Preliminary Report on Patentability with Written Opinion (PCT/US2015/054693), dated Apr. 11, 2017, 6 pages.
Uniprot protein database, Q9NP55, BBPI fold-containing family A member 1, *Homo sapiens* (Human); Accessed on Apr. 20, 2017.
U.S. Appl. No. 13/321,617, filed Nov. 21, 2011; Office Action dated May 18, 2016.
U.S. Appl. No. 14/971,523, filed Dec. 16, 2015; Office Action dated Oct. 14, 2016.
U.S. Appl. No. 14/971,523, filed Dec. 16, 2015; Office Action dated May 5, 2016.
Notification of Transmittal of the International Search Report and the Written Opinion of the International Searching Authority, or the Declaration corresponding to International Application No. PCT/US2015/054693 dated Jan. 21, 2016.
Bingle et al., "PLUNC: a novel family of candidate host defence proteins expressed in the upper airways and nasopharynx," Hum. Mol. Genet. 11: 937-943 (2002).
Bingle et al., "Phylogenetic and evolutionary analysis of the PLUNC gene family." Protein Sci. 13: 422-430 (2004).
Bingle et al., "Characterisation of the human plunc gene, a gene product with an upper airways and nasopharyngeal restricted expression pattern," Biochim. Biophys. Acta 1493:363-367 (2000).
Gaillard et al., The Soluble Protein SPLUNC1 Regulates ENaC in Human Bronchial Epithelial Cell Cultures, presented at the 2007 North American Cystic Fibrosis Conference (Oct. 4, 2007).

(Continued)

*Primary Examiner* — John D Ulm
(74) *Attorney, Agent, or Firm* — McDermott Will & Emery LLP

(57) ABSTRACT

The present invention relates to the ability of specialized non-naturally occurring peptides to bind to sodium channels and inhibit activation of the sodium channels. The invention further relates to methods for regulating of sodium absorption and fluid volume and treating disorders responsive to modulating sodium absorption by modulating the binding of specialized non-naturally occurring peptides to sodium channels.

18 Claims, 31 Drawing Sheets

Specification includes a Sequence Listing.

(56) References Cited

OTHER PUBLICATIONS

Garcia-Caballero et al., "ENaC proteolytic regulation by channel-activating protease 2," J. Gen. Physiol. 132:521-535 (2008).
Passero et al., "Plasmin activates epithelial Na+ channels by cleaving they subunit," J. Biol. Chem. 283:36586-36591 (2008).
Pochynyuk et al., Binding and direct activation of the epithelial Na+ channel (ENaC) by phosphatidylinositides, J. Physiol. 580:365-372 (2007).
Schreiber et al., "The first-nucleotide binding domain of the cystic-fibrosis transmembrane conductance regulator is important for inhibition of the epithelial Na+ channel," Proc. Natl. Acad. Sci. USA 96:5310-5315 (1999).
Lee, Bo-Young, "Genome-wide association study of copy number variations associated with pulmonary function measures in Korea Associated Resource (KARE) cohorts", Genomics, 97 101-105 (2011).
BPI fold-containing family A member 1, Uniprot database, Protein Accession Q9NP55, pp. 1-10, accessed on Apr. 20, 2017.
U.S. Appl. No. 14/345,975, filed Mar. 20, 2014, Office Action dated Jun. 23, 2014.
Araga et al., "A complementary peptide vaccine that induces T. cell anergy and prevents experimental allergic neuritis in Lewis rats," J. Immunol. 163:476-482 (1999).
Denac et al., "Structure, function and pharmacology of voltage-gated sodium channels," Naunyn-Schmiedeberg's Archives of Pharmacology 362:453-479 (2000).
Rollins, "Regulation of the epithelial sodium channel (ENaC) by the Short Palate, Lung, and Nasal Epithelial Clone (SPLUNC1)," Master's Thesis, Sep. 2010.
U.S. Appl. No. 14/345,975, filed Mar. 20, 2014; Office Action dated Jan. 9, 2015.
International Search Report and Written Opinion Corresponding to International Application No. PCT/US2010/036531; dated Feb. 18, 2011; 14 Pages.
International Preliminary Report on Patentability Corresponding to International Application No. PCT/US2010/036531; dated Dec. 8, 2011; 8 Pages.
International Search Report and Written Opinion Corresponding to International Application No. PCT/US2012/056112; dated Jan. 11, 2013; 9 Pages.
International Preliminary Report on Patentability Corresponding to International Application No. PCT/US2012/056112; dated Apr. 3, 2014; 7 Pages.
Daviskas et al. "Mucociliary clearance in patients with chronic asthma: effects of beta agonists", Respirology 10:426-435 (2005).
Daviskas et al. "Hyperosmolar Agents and Clearance of Mucus in the Diseased Airway", J. Aerosol Medicine 19(1):100-109 (2006).
Daviskas et al. "Inhaled mannitol changes the sputum properties in asthmatics with mucus hypersecretion", Respirology 12:683-691 (2007).
Kunzelmann et al. "Electrolyte Transport in the Mammalian Colon: Mechanisms and Implications for Disease", Phvsiol. Rev. 82:245-289 (2002).
Mall et al. "Development of Chronic Bronchitis and Emphysema in 13-Epithelial Na+ Channel-Overexpressing Mice", Am. J. Resoir. Crit. Care Med. 177:730-742 (2008).
Gaillard et al. "Regulation of the epithelial Na+ channel and airway surface liquid volume by serine proteases", Pflugers Arch—Eur J Physiol 460: 1-17 (2010).
Garcia-Caballero et al. "Correction for 'SPLUNC1 regulates airway surface liquid volume by protecting ENaC from proteolytic cleavage", PNAS 106: 11412-11417 (2009).
Rollins et al. "SPLUNC1 expression reduces surface levels of the epithelial sodium channel (ENaC) in Xenopus laevis oocytes", Channels 4(4):255-259 (2010).
Extended European Search Report corresponding to European Application No. 12833524.7 dated Jun. 29, 2015.
U.S. Appl. No. 13/321,617, filed Jan. 26, 2012; Non-Final Office Action dated Jun. 18, 2013.
U.S. Appl. No. 13/321,617, filed Jan. 26, 2012; Final Office Action dated Jan. 29, 2014.
U.S. Appl. No. 13/321,617, filed Jan. 26, 2012; Non-Final Office Action dated Sep. 11, 2014.
U.S. Appl. No. 13/321,617, filed Jan. 26, 2012; Non-Final Office Action dated Jan. 14, 2015.
U.S. Appl. No. 13/321,617, filed Jan. 26, 2012; Non-Final Office Action dated Aug. 25, 2015.

\* cited by examiner

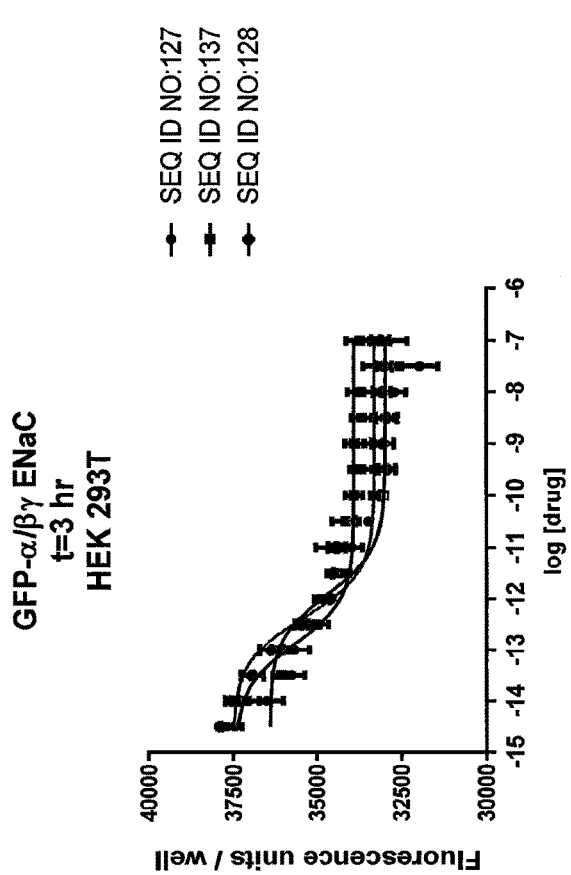

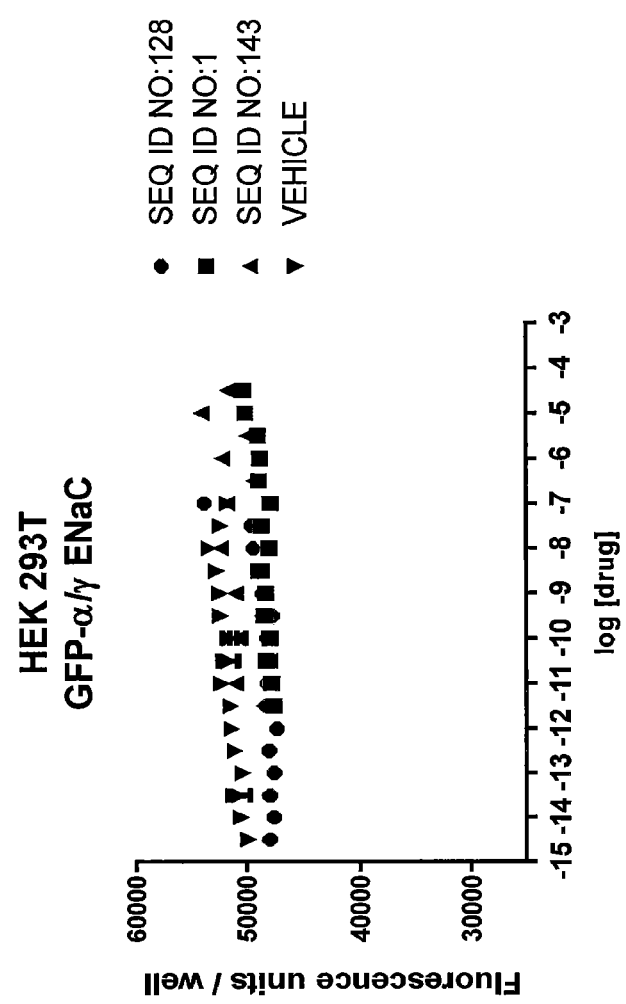

SEQUENCE LISTING

```
<160> NUMBER OF SEQ ID NOS: 144

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 1

Gly Gly Leu Pro Val Pro Leu Asp Gln Thr Leu Pro Leu Asn Val Asn
1               5                   10                  15

Pro Ala

<210> SEQ ID NO 2
<211> LENGTH: 19
<212> TYPE: PRT
<213> ORGANISM: Artificial Sequence
<220> FEATURE:
```

```
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(2)
<223> OTHER INFORMATION: d-Ala
<220> FEATURE:
<221> NAME/KEY: MOD_RES
<222> LOCATION: (18)..(19)
<223> OTHER INFORMATION: d-Ala
<220> FEATURE:
<223> OTHER INFORMATION: C-term Amidation

<400> SEQUENCE: 2

Ala Ala Leu Pro Val Pro Leu Asp Gln Thr Leu Pro Leu Asn Val Asn
1               5                   10                  15

Pro Ala Ala

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(2)
<223> OTHER INFORMATION: D-Ala
<220> FEATURE:
<221> NAME/KEY: MOD_RES
<222> LOCATION: (11)..(12)
<223> OTHER INFORMATION: D-Ala
<220> FEATURE:
<223> OTHER INFORMATION: C-term Amidation

<400> SEQUENCE: 3

Ala Ala Leu Pro Val Pro Leu Asp Gln Thr Ala Ala
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(2)
<223> OTHER INFORMATION: D-Ala
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (11)..(12)
<223> OTHER INFORMATION: D-Ala
<220> FEATURE:
<223> OTHER INFORMATION: C-term Amidation

<400> SEQUENCE: 4

Ala Ala Leu Pro Val Pro Leu Asp Gln Thr Ala Ala
1               5                   10

<210> SEQ ID NO 5
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(2)
<223> OTHER INFORMATION: D-Ala
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (11)..(12)
<223> OTHER INFORMATION: D-Ala
<220> FEATURE:
<223> OTHER INFORMATION: C-term Amidation

<400> SEQUENCE: 5

Ala Ala Leu Pro Leu Pro Leu Asp Gln Thr Ala Ala
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(2)
<223> OTHER INFORMATION: D-Ala
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (11)..(12)
<223> OTHER INFORMATION: D-Ala
<220> FEATURE:
<223> OTHER INFORMATION: C-term Amidation

<400> SEQUENCE: 6

Ala Ala Leu Pro Val Pro Leu Asp Gln Thr Ala Ala
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(2)
<223> OTHER INFORMATION: D-Ala
<220> FEATURE:
<221> NAME/KEY: MOD_RES
<222> LOCATION: (11)..(12)
<223> OTHER INFORMATION: D-Ala
<220> FEATURE:
<223> OTHER INFORMATION: C-term Amidation

<400> SEQUENCE: 7

Ala Ala Leu Pro Val Pro Leu Asp Asn Thr Ala Ala
1               5                   10
```

```
<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(2)
<223> OTHER INFORMATION: D-Ala
<220> FEATURE:
<221> NAME/KEY: MOD_RES
<222> LOCATION: (11)..(12)
<223> OTHER INFORMATION: D-Ala
<220> FEATURE:
<223> OTHER INFORMATION: C-term Amidation

<400> SEQUENCE: 8

Ala Ala Leu Pro Val Pro Leu Glu Gln Thr Ala Ala
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(2)
<223> OTHER INFORMATION: D-Ala
<220> FEATURE:
<221> NAME/KEY: MOD_RES
<222> LOCATION: (11)..(12)
<223> OTHER INFORMATION: D-Ala
<220> FEATURE:
<223> OTHER INFORMATION: C-term Amidation

<400> SEQUENCE: 9

Ala Ala Leu Pro Val Pro Leu Asp Gln Ser Ala Ala
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 10

Leu Pro Val Pro Leu Asp Gln Thr
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
```

```
<223> OTHER INFORMATION: N-term Acetylation
<220> FEATURE:
<221> NAME/KEY: MOD_RES
<222> LOCATION: (2)..(2)
<223> OTHER INFORMATION: 3,4-dehydro-L-Proline
<220> FEATURE:
<223> OTHER INFORMATION: C-term Amidation

<400> SEQUENCE: 11

Leu Pro Val Pro Leu Asp Gln Thr
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (4)..(4)
<223> OTHER INFORMATION: 3,4-dehydro-L-Proline
<220> FEATURE:
<223> OTHER INFORMATION: C-term Amidation

<400> SEQUENCE: 12

Leu Pro Val Pro Leu Asp Gln Thr
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: 3,4-dehydro-L-Proline
<220> FEATURE:
<221> NAME/KEY: MOD_RES
<222> LOCATION: (4)..(4)
<223> OTHER INFORMATION: 3,4-dehydro-L-Proline
<220> FEATURE:
<223> OTHER INFORMATION: C-term Amidation

<400> SEQUENCE: 13

Leu Pro Val Pro Leu Asp Gln Thr
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: (2R,5S)-5-phenyl-pyrrolidine-2-carboxylic acid
<220> FEATURE:
<223> OTHER INFORMATION: C-term Amidation

<400> SEQUENCE: 14

Leu Xaa Val Pro Leu Asp Gln Thr
1               5
```

```
<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (4)..(4)
<223> OTHER INFORMATION: (2R,5S)-5-phenyl-pyrrolidine-2-carboxylic acid
<220> FEATURE:
<223> OTHER INFORMATION: C-term Amidation

<400> SEQUENCE: 15

Leu Pro Val Xaa Leu Asp Gln Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: 4-hydroxyproline
<220> FEATURE:
<223> OTHER INFORMATION: C-term Amidation

<400> SEQUENCE: 16

Leu Pro Val Pro Leu Asp Gln Thr
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 17

Leu Pro Val Pro Leu Asp Gln Thr
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: 4-hydroxyproline
<220> FEATURE:
<221> NAME/KEY: MOD_RES
```

```
<222> LOCATION: (4)..(4)
<223> OTHER INFORMATION: 4-hydroxyproline
<220> FEATURE:
<223> OTHER INFORMATION: C-term Amidation

<400> SEQUENCE: 18

Leu Pro Val Pro Leu Asp Gln Thr
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 19

Leu Pro Val Pro Leu Glu Gln Ser
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (8)..(8)
<223> OTHER INFORMATION: L-alpha-methylserine
<220> FEATURE:
<223> OTHER INFORMATION: C-term Amidation

<400> SEQUENCE: 20

Leu Pro Val Pro Leu Glu Gln Ser
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 21

Leu Pro Val Pro Val Asp Gln Thr
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 22
```

```
Leu Pro Val Pro Val Glu Gln Ser
1               5
```

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 23

```
Leu Pro Val Pro Val Asp Gln Ser
1               5
```

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 24

```
Val Pro Val Pro Leu Asp Gln Thr
1               5
```

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 25

```
Leu Pro Leu Pro Leu Asp Gln Ser
1               5
```

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 26

```
Val Pro Leu Pro Leu Asp Gln Ser
1               5
```

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting

```
      peptide sequence
<220> FEATURE:
<223> OTHER INFORMATION: C-term Amidation

<400> SEQUENCE: 27

Leu Pro Leu Pro Leu Asp Gln Thr
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: 4-hydroxyproline
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 28

Val Pro Leu Pro Val Glu Gln Ser
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 29

Val Pro Leu Pro Val Glu Gln Ser
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 30

Leu Pro Leu Pro Leu Glu Gln Ser
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
```

```
<222> LOCATION: (3)..(3)
<223> OTHER INFORMATION: N-methylvaline
<220> FEATURE:
<223> OTHER INFORMATION: C-term Amidation

<400> SEQUENCE: 31

Leu Pro Val Pro Leu Asp Gln Ser
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (3)..(3)
<223> OTHER INFORMATION: Norleucine
<220> FEATURE:
<223> OTHER INFORMATION: C-term Amidation

<400> SEQUENCE: 32

Leu Pro Leu Pro Leu Asp Gln Thr
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (3)..(3)
<223> OTHER INFORMATION: Norleucine
<220> FEATURE:
<223> OTHER INFORMATION: C-term Amidation

<400> SEQUENCE: 33

Leu Pro Leu Pro Val Glu Gln Ser
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (3)..(3)
<223> OTHER INFORMATION: Norleucine
<220> FEATURE:
<223> OTHER INFORMATION: C-term Amidation

<400> SEQUENCE: 34

Leu Pro Leu Pro Val Glu Gln Ser
1               5

<210> SEQ ID NO 35
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: 4-hydroxyproline
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 35

Leu Pro Leu Pro Leu Glu Gln Ser
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: 4-hydroxyproline
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 36

Leu Pro Leu Pro Val Glu Gln Ser
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (4)..(4)
<223> OTHER INFORMATION: 3,4-dehydro-L-Proline
<220> FEATURE:
<223> OTHER INFORMATION: C-term Amidation

<400> SEQUENCE: 37

Leu Pro Val Pro Leu Asp Gln Thr
1               5

<210> SEQ ID NO 38
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (2)..(2)
<223> OTHER INFORMATION: 3,4-dehydro-L-Proline
<220> FEATURE:
<221> NAME/KEY: MOD_RES
<222> LOCATION: (4)..(4)
<223> OTHER INFORMATION: 3,4-dehydro-L-Proline
<220> FEATURE:
<223> OTHER INFORMATION: C-term Amidation

<400> SEQUENCE: 38

Leu Pro Val Pro Leu Asp Gln Thr
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (2)..(2)
<223> OTHER INFORMATION: (2R,5S)-5-phenyl-pyrrolidine-2-carboxylic acid
<220> FEATURE:
<223> OTHER INFORMATION: C-term Amidation

<400> SEQUENCE: 39

Leu Xaa Val Pro Leu Asp Gln Thr
1               5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (4)..(4)
<223> OTHER INFORMATION: (2R,5S)-5-phenyl-pyrrolidine-2-carboxylic acid
<220> FEATURE:
<223> OTHER INFORMATION: C-term Amidation

<400> SEQUENCE: 40

Leu Pro Val Xaa Leu Asp Gln Thr
1               5

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
```

```
<223> OTHER INFORMATION: N-term Acetylation
<220> FEATURE:
<221> NAME/KEY: MOD_RES
<222> LOCATION: (2)..(2)
<223> OTHER INFORMATION: 4-hydroxyproline
<220> FEATURE:
<223> OTHER INFORMATION: C-term Amidation

<400> SEQUENCE: 41

Leu Pro Val Pro Leu Asp Gln Thr
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 42

Leu Pro Val Pro Leu Asp Gln Thr
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (2)..(2)
<223> OTHER INFORMATION: 4-hydroxyproline
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 43

Leu Pro Val Pro Leu Asp Gln Thr
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 44
```

```
Leu Pro Val Pro Leu Glu Gln Ser
1               5
```

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (8)..(8)
<223> OTHER INFORMATION: L-alpha-methylserine
<220> FEATURE:
<223> OTHER INFORMATION: C-term Amidation

<400> SEQUENCE: 45

```
Leu Pro Val Pro Leu Glu Gln Ser
1               5
```

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 46

```
Leu Pro Val Pro Val Asp Gln Thr
1               5
```

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 47

```
Leu Pro Val Pro Val Glu Gln Ser
1               5
```

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 48

Leu Pro Val Pro Val Asp Gln Ser
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 49

Val Pro Val Pro Leu Asp Gln Thr
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 50

Leu Pro Leu Pro Leu Asp Gln Ser
1               5

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 51

Val Pro Leu Pro Leu Asp Gln Ser
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 52

Leu Pro Leu Pro Leu Asp Gln Thr
1               5

```
<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (2)..(2)
<223> OTHER INFORMATION: 4-hydroxyproline
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 53

Val Pro Leu Pro Val Glu Gln Ser
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 54

Val Pro Leu Pro Val Glu Gln Ser
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 55

Leu Pro Leu Pro Leu Glu Gln Ser
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
```

```
<222> LOCATION: (3)..(3)
<223> OTHER INFORMATION: N-methylvaline
<220> FEATURE:
<223> OTHER INFORMATION: C-term Amidation

<400> SEQUENCE: 56

Leu Pro Val Pro Leu Asp Gln Ser
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (3)..(3)
<223> OTHER INFORMATION: Norleucine
<220> FEATURE:
<223> OTHER INFORMATION: C-term Amidation

<400> SEQUENCE: 57

Leu Pro Leu Pro Leu Asp Gln Thr
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (3)..(3)
<223> OTHER INFORMATION: Norleucine
<220> FEATURE:
<223> OTHER INFORMATION: C-term Amidation

<400> SEQUENCE: 58

Leu Pro Leu Pro Val Glu Gln Ser
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (3)..(3)
<223> OTHER INFORMATION: Norleucine
<220> FEATURE:
<223> OTHER INFORMATION: C-term Amidation

<400> SEQUENCE: 59

Leu Pro Leu Pro Val Glu Gln Ser
1               5
```

```
<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (2)..(2)
<223> OTHER INFORMATION: 4-hydroxyproline
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 60

Leu Pro Leu Pro Leu Glu Gln Ser
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (2)..(2)
<223> OTHER INFORMATION: 4-hydroxyproline
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 61

Leu Pro Leu Pro Val Glu Gln Ser
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (2)..(2)
<223> OTHER INFORMATION: 3,4-dehydro-L-Proline
<220> FEATURE:
<223> OTHER INFORMATION: C-term Amidation
```

```
<400> SEQUENCE: 62

Leu Pro Val Pro Leu Asp Gln Thr
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (4)..(4)
<223> OTHER INFORMATION: 3,4-dehydro-L-Proline
<220> FEATURE:
<223> OTHER INFORMATION: C-term Amidation

<400> SEQUENCE: 63

Leu Pro Val Pro Leu Asp Gln Thr
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: 3,4-dehydro-L-Proline
<220> FEATURE:
<221> NAME/KEY: MOD_RES
<222> LOCATION: (4)..(4)
<223> OTHER INFORMATION: 3,4-dehydro-L-Proline
<220> FEATURE:
<223> OTHER INFORMATION: C-term Amidation

<400> SEQUENCE: 64

Leu Pro Val Pro Leu Asp Gln Thr
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: (2R,5S)-5-phenyl-pyrrolidine-2-carboxylic acid
<220> FEATURE:
<223> OTHER INFORMATION: C-term Amidation

<400> SEQUENCE: 65

Leu Xaa Val Pro Leu Asp Gln Thr
1               5

<210> SEQ ID NO 66
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (4)..(4)
<223> OTHER INFORMATION: (2R,5S)-5-phenyl-pyrrolidine-2-carboxylic acid
<220> FEATURE:
<223> OTHER INFORMATION: C-term Amidation

<400> SEQUENCE: 66

Leu Pro Val Xaa Leu Asp Gln Thr
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: 4-hydroxyproline
<220> FEATURE:
<223> OTHER INFORMATION: C-term Amidation

<400> SEQUENCE: 67

Leu Pro Val Pro Leu Asp Gln Thr
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 68

Leu Pro Val Pro Leu Asp Gln Thr
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: 4-hydroxyproline
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 69
```

Leu Pro Val Pro Leu Asp Gln Thr
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 70

Leu Pro Val Pro Leu Glu Gln Ser
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (8)..(8)
<223> OTHER INFORMATION: L-alpha-methylserine
<220> FEATURE:
<223> OTHER INFORMATION: C-term Amidation

<400> SEQUENCE: 71

Leu Pro Val Pro Leu Glu Gln Ser
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 72

Leu Pro Val Pro Val Asp Gln Thr
1               5

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 73

Leu Pro Val Pro Val Glu Gln Ser
1               5

<210> SEQ ID NO 74
<211> LENGTH: 8
<212> TYPE: PRT

```
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 74

Leu Pro Val Pro Val Asp Gln Ser
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 75

Val Pro Val Pro Leu Asp Gln Thr
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 76

Leu Pro Leu Pro Leu Asp Gln Ser
1               5

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 77

Val Pro Leu Pro Leu Asp Gln Ser
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 78

Leu Pro Leu Pro Leu Asp Gln Thr
```

```
<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: 4-hydroxyproline
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 79

Val Pro Leu Pro Val Glu Gln Ser
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 80

Val Pro Leu Pro Val Glu Gln Ser
1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 81

Leu Pro Leu Pro Leu Glu Gln Ser
1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (3)..(3)
<223> OTHER INFORMATION: N-methylvaline
<220> FEATURE:
<223> OTHER INFORMATION: C-term Amidation

<400> SEQUENCE: 82
```

```
Leu Pro Val Pro Leu Asp Gln Ser
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (3)..(3)
<223> OTHER INFORMATION: Norleucine
<220> FEATURE:
<223> OTHER INFORMATION: C-term Amidation

<400> SEQUENCE: 83

Leu Pro Leu Pro Leu Asp Gln Thr
1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (3)..(3)
<223> OTHER INFORMATION: Norleucine
<220> FEATURE:
<223> OTHER INFORMATION: C-term Amidation

<400> SEQUENCE: 84

Leu Pro Leu Pro Val Glu Gln Ser
1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (3)..(3)
<223> OTHER INFORMATION: Norleucine
<220> FEATURE:
<223> OTHER INFORMATION: C-term Amidation

<400> SEQUENCE: 85

Leu Pro Leu Pro Val Glu Gln Ser
1               5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: 4-hydroxyproline
```

```
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 86

Leu Pro Leu Pro Leu Glu Gln Ser
1               5

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: 4-hydroxyproline
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 87

Leu Pro Leu Pro Val Glu Gln Ser
1               5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (4)..(4)
<223> OTHER INFORMATION: 3,4-dehydro-L-Proline
<220> FEATURE:
<223> OTHER INFORMATION: C-term Amidation

<400> SEQUENCE: 88

Leu Pro Val Pro Leu Asp Gln Thr
1               5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
```

```
<220> FEATURE:
<221> NAME/KEY: MOD_RES
<222> LOCATION: (2)..(2)
<223> OTHER INFORMATION: 3,4-dehydro-L-Proline
<220> FEATURE:
<221> NAME/KEY: MOD_RES
<222> LOCATION: (4)..(4)
<223> OTHER INFORMATION: 3,4-dehydro-L-Proline
<220> FEATURE:
<223> OTHER INFORMATION: C-term Amidation

<400> SEQUENCE: 89

Leu Pro Val Pro Leu Asp Gln Thr
1               5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (2)..(2)
<223> OTHER INFORMATION: (2R,5S)-5-phenyl-pyrrolidine-2-carboxylic acid
<220> FEATURE:
<223> OTHER INFORMATION: C-term Amidation

<400> SEQUENCE: 90

Leu Xaa Val Pro Leu Asp Gln Thr
1               5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (4)..(4)
<223> OTHER INFORMATION: (2R,5S)-5-phenyl-pyrrolidine-2-carboxylic acid
<220> FEATURE:
<223> OTHER INFORMATION: C-term Amidation

<400> SEQUENCE: 91

Leu Pro Val Xaa Leu Asp Gln Thr
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (2)..(2)
<223> OTHER INFORMATION: 4-hydroxyproline
<220> FEATURE:
<223> OTHER INFORMATION: C-term Amidation
```

<400> SEQUENCE: 92

Leu Pro Val Pro Leu Asp Gln Thr
1               5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 93

Leu Pro Val Pro Leu Asp Gln Thr
1               5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (2)..(2)
<223> OTHER INFORMATION: 4-hydroxyproline
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 94

Leu Pro Val Pro Leu Asp Gln Thr
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 95

Leu Pro Val Pro Leu Glu Gln Ser
1               5

<210> SEQ ID NO 96
<211> LENGTH: 8
<212> TYPE: PRT

```
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (8)..(8)
<223> OTHER INFORMATION: L-alpha-methylserine
<220> FEATURE:
<223> OTHER INFORMATION: C-term Amidation

<400> SEQUENCE: 96

Leu Pro Val Pro Leu Glu Gln Ser
1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 97

Leu Pro Val Pro Val Asp Gln Thr
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 98

Leu Pro Val Pro Val Glu Gln Ser
1               5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 99

Leu Pro Val Pro Val Asp Gln Ser
1               5

<210> SEQ ID NO 100
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 100

Val Pro Val Pro Leu Asp Gln Thr
1               5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 101

Leu Pro Leu Pro Leu Asp Gln Ser
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 102

Val Pro Leu Pro Leu Asp Gln Ser
1               5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 103

Leu Pro Leu Pro Leu Asp Gln Thr
1               5

<210> SEQ ID NO 104
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (2)..(2)
<223> OTHER INFORMATION: 4-hydroxyproline
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 104

Val Pro Leu Pro Val Glu Gln Ser
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 105

Val Pro Leu Pro Val Glu Gln Ser
1               5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<223> OTHER INFORMATION: C-term Amidation

<400> SEQUENCE: 106

Leu Pro Leu Pro Leu Glu Gln Ser
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (3)..(3)
<223> OTHER INFORMATION: N-methylvaline
<220> FEATURE:
<223> OTHER INFORMATION: C-term Amidation

<400> SEQUENCE: 107
```

Leu Pro Val Pro Leu Asp Gln Ser
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (3)..(3)
<223> OTHER INFORMATION: Norleucine
<220> FEATURE:
<223> OTHER INFORMATION: C-term Amidation

<400> SEQUENCE: 108

Leu Pro Leu Pro Leu Asp Gln Thr
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (3)..(3)
<223> OTHER INFORMATION: Norleucine
<220> FEATURE:
<223> OTHER INFORMATION: C-term Amidation

<400> SEQUENCE: 109

Leu Pro Leu Pro Val Glu Gln Ser
1               5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: N-term Acetylation
<220> FEATURE:
<221> NAME/KEY: MOD_RES
<222> LOCATION: (3)..(3)
<223> OTHER INFORMATION: Norleucine
<220> FEATURE:
<223> OTHER INFORMATION: C-term Amidation

<400> SEQUENCE: 110

Leu Pro Leu Pro Val Glu Gln Ser
1               5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic

```
        Sodium channel activity inhibiting
        peptide sequence
<220> FEATURE:
<223> OTHER INFORMATION: N-term Acetylation
<220> FEATURE:
<221> NAME/KEY: MOD_RES
<222> LOCATION: (2)..(2)
<223> OTHER INFORMATION: 4-hydroxyproline
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 111

Leu Pro Leu Pro Leu Glu Gln Ser
1               5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
        Sodium channel activity inhibiting
        peptide sequence
<220> FEATURE:
<223> OTHER INFORMATION: N-term Acetylation
<220> FEATURE:
<221> NAME/KEY: MOD_RES
<222> LOCATION: (2)..(2)
<223> OTHER INFORMATION: 4-hydroxyproline
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: 4-hydroxyproline
<220> FEATURE:
<223> OTHER INFORMATION: C-term Amidation

<400> SEQUENCE: 112

Leu Pro Leu Pro Val Glu Gln Ser
1               5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
        Sodium channel activity inhibiting
        peptide sequence
<220> FEATURE:
<223> OTHER INFORMATION: C-term Amidation

<400> SEQUENCE: 113

Leu Pro Val Pro Leu Asp Gln Thr
1               5

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
```

Sodium channel activity inhibiting
peptide sequence
<220> FEATURE:
<223> OTHER INFORMATION: C-term Amidation

<400> SEQUENCE: 114

Asp Gln Thr Leu Pro Leu Asn Val Asn Pro
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 115

Leu Pro Val Pro Leu Asp Gln Thr Leu Pro Leu
1               5                   10

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(1)
<223> OTHER INFORMATION: Leu or a conservative substitution with a
      natural or non-natural amino acid
<220> FEATURE:
<221> NAME/KEY: MOD_RES
<222> LOCATION: (2)..(2)
<223> OTHER INFORMATION: Pro or a conservative substitution with a
      natural or non-natural amino acid
<220> FEATURE:
<221> NAME/KEY: MOD_RES
<222> LOCATION: (3)..(3)
<223> OTHER INFORMATION: Val or a conservative substitution with a
      natural or non-natural amino acid
<220> FEATURE:
<221> NAME/KEY: MOD_RES
<222> LOCATION: (4)..(4)
<223> OTHER INFORMATION: Pro or a conservative substitution with a
      natural or non-natural amino acid
<220> FEATURE:
<221> NAME/KEY: MOD_RES
<222> LOCATION: (5)..(5)
<223> OTHER INFORMATION: Leu or a conservative substitution with a
      natural or non-natural amino acid
<220> FEATURE:
<221> NAME/KEY: MOD_RES
<222> LOCATION: (6)..(6)
<223> OTHER INFORMATION: Asp or a conservative substitution with a
      natural or non-natural amino acid
<220> FEATURE:
<221> NAME/KEY: MOD_RES
<222> LOCATION: (7)..(7)
<223> OTHER INFORMATION: Gln or a conservative substitution with a
      natural or non-natural amino acid
<220> FEATURE:
<221> NAME/KEY: MOD_RES
<222> LOCATION: (8)..(8)
<223> OTHER INFORMATION: Thr or a conservative substitution with a
      natural or non-natural amino acid
<220> FEATURE:
<223> OTHER INFORMATION: C-term Amidation

```
<400> SEQUENCE: 116

Xaa Xaa Xaa Xaa Xaa Xaa Xaa Xaa
1               5

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(1)
<223> OTHER INFORMATION: Leu, Norleucine or Val
<220> FEATURE:
<221> NAME/KEY: MOD_RES
<222> LOCATION: (2)..(2)
<223> OTHER INFORMATION: Pro, 4-hydroxyproline, (2R,5S)-5-phenyl-
      pyrrolidine-2-carboxylic acid or 3,4-dehydro-L-Proline
<220> FEATURE:
<221> NAME/KEY: MOD_RES
<222> LOCATION: (3)..(3)
<223> OTHER INFORMATION: Val, Leu, Norleucine or N-methylvaline
<220> FEATURE:
<221> NAME/KEY: MOD_RES
<222> LOCATION: (4)..(4)
<223> OTHER INFORMATION: Pro, 4-hydroxyproline, (2R,5S)-5-phenyl-
      pyrrolidine-2-carboxylic acid or 3,4-dehydro-L-Proline
<220> FEATURE:
<221> NAME/KEY: MOD_RES
<222> LOCATION: (5)..(5)
<223> OTHER INFORMATION: Leu, Norleucine or Val
<220> FEATURE:
<221> NAME/KEY: MOD_RES
<222> LOCATION: (6)..(6)
<223> OTHER INFORMATION: Asp or Glu
<220> FEATURE:
<221> NAME/KEY: MOD_RES
<222> LOCATION: (7)..(7)
<223> OTHER INFORMATION: Gln or Asn
<220> FEATURE:
<221> NAME/KEY: MOD_RES
<222> LOCATION: (8)..(8)
<223> OTHER INFORMATION: Thr, Ser or L-alpha-methylserine
<220> FEATURE:
<223> OTHER INFORMATION: C-term Amidation

<400> SEQUENCE: 117

Xaa Xaa Xaa Xaa Xaa Xaa Xaa Xaa
1               5

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(1)
<223> OTHER INFORMATION: Leu or a conservative substitution with a
      natural or non-natural amino acid
<220> FEATURE:
<221> NAME/KEY: MOD_RES
<222> LOCATION: (2)..(2)
<223> OTHER INFORMATION: Pro or a conservative substitution with a
      natural or non-natural amino acid
<220> FEATURE:
<221> NAME/KEY: MOD_RES
<222> LOCATION: (3)..(3)
<223> OTHER INFORMATION: Val or a conservative substitution with a
```

-continued

```
        natural or non-natural amino acid
<220> FEATURE:
<221> NAME/KEY: MOD_RES
<222> LOCATION: (4)..(4)
<223> OTHER INFORMATION: Pro or a conservative substitution with a
        natural or non-natural amino acid
<220> FEATURE:
<221> NAME/KEY: MOD_RES
<222> LOCATION: (5)..(5)
<223> OTHER INFORMATION: Leu or a conservative substitution with a
        natural or non-natural amino acid
<220> FEATURE:
<221> NAME/KEY: MOD_RES
<222> LOCATION: (6)..(6)
<223> OTHER INFORMATION: Asp or a conservative substitution with a
        natural or non-natural amino acid
<220> FEATURE:
<221> NAME/KEY: MOD_RES
<222> LOCATION: (7)..(7)
<223> OTHER INFORMATION: Gln or a conservative substitution with a
        natural or non-natural amino acid
<220> FEATURE:
<221> NAME/KEY: MOD_RES
<222> LOCATION: (8)..(8)
<223> OTHER INFORMATION: Thr or a conservative substitution with a
        natural or non-natural amino acid
<220> FEATURE:
<221> NAME/KEY: MOD_RES
<222> LOCATION: (9)..(9)
<223> OTHER INFORMATION: Thr or a conservative substitution with a
        natural or non-natural amino acid
<220> FEATURE:
<221> NAME/KEY: MOD_RES
<222> LOCATION: (10)..(10)
<223> OTHER INFORMATION: Leu or a conservative substitution with a
        natural or non-natural amino acid
<220> FEATURE:
<221> NAME/KEY: MOD_RES
<222> LOCATION: (11)..(11)
<223> OTHER INFORMATION: Pro or a conservative substitution with a
        natural or non-natural amino acid
<220> FEATURE:
<221> NAME/KEY: MOD_RES
<222> LOCATION: (12)..(12)
<223> OTHER INFORMATION: ASn or a conservative substitution with a
        natural or non-natural amino acid
<220> FEATURE:
<221> NAME/KEY: MOD_RES
<222> LOCATION: (13)..(13)
<223> OTHER INFORMATION: Val or a conservative substitution with a
        natural or non-natural amino acid
<220> FEATURE:
<221> NAME/KEY: MOD_RES
<222> LOCATION: (14)..(14)
<223> OTHER INFORMATION: Asn or a conservative substitution with a
        natural or non-natural amino acid
<220> FEATURE:
<221> NAME/KEY: MOD_RES
<222> LOCATION: (15)..(15)
<223> OTHER INFORMATION: Pro or a conservative substitution with a
        natural or non-natural amino acid
<220> FEATURE:
<223> OTHER INFORMATION: C-term Amidation

<400> SEQUENCE: 118

Xaa Xaa Xaa Xaa Xaa Xaa Xaa Xaa Xaa Xaa Xaa Xaa Xaa Xaa Xaa
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Description of Artificial Sequence: Synthetic
        Sodium channel activity inhibiting
        peptide sequence
<220> FEATURE:
```

```
<223> OTHER INFORMATION: C-term Amidation

<400> SEQUENCE: 119

Leu Pro Val Pro Leu Asp Gln Thr Leu Pro Leu Asn Val Asn Pro
1               5                   10                  15

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 120

Leu Pro Val Pro Leu Asp Gln Thr
1               5

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(1)
<223> OTHER INFORMATION: Norleucine
<220> FEATURE:
<223> OTHER INFORMATION: C-term Amidation

<400> SEQUENCE: 121

Leu Pro Val Pro Leu Asp Gln Thr
1               5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (3)..(3)
<223> OTHER INFORMATION: Norleucine
<220> FEATURE:
<223> OTHER INFORMATION: C-term Amidation

<400> SEQUENCE: 122

Leu Pro Leu Pro Leu Asp Gln Thr
1               5

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (5)..(5)
<223> OTHER INFORMATION: Norleucine
```

```
<220> FEATURE:
<223> OTHER INFORMATION: C-term Amidation

<400> SEQUENCE: 123

Leu Pro Val Pro Leu Asp Gln Thr
1               5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 124

Leu Pro Val Pro Leu Asp Asn Thr
1               5

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 125

Leu Pro Val Pro Leu Glu Gln Thr
1               5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 126

Leu Pro Val Pro Leu Asp Gln Ser
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 127

Leu Pro Ile Pro Leu Asp Gln Thr
1               5

<210> SEQ ID NO 128
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(2)
<223> OTHER INFORMATION: D-Ala
<220> FEATURE:
<221> NAME/KEY: MOD_RES
<222> LOCATION: (11)..(12)
<223> OTHER INFORMATION: D-Ala
<220> FEATURE:
<223> OTHER INFORMATION: C-term Amidation

<400> SEQUENCE: 128

Ala Ala Leu Pro Ile Pro Leu Asp Gln Thr Ala Ala
1               5                   10

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (3)..(3)
<223> OTHER INFORMATION: Aminoheptanoic acid
<220> FEATURE:
<223> OTHER INFORMATION: C-term Amidation

<400> SEQUENCE: 129

Leu Pro Xaa Pro Leu Asp Gln Thr
1               5

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 130

Leu Pro Phe Pro Leu Asp Gln Thr
1               5

<210> SEQ ID NO 131
<211> LENGTH: 12
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(2)
<223> OTHER INFORMATION: D-Ala
<220> FEATURE:
<221> NAME/KEY: MOD_RES
<222> LOCATION: (4)..(4)
<223> OTHER INFORMATION: 4-hydroxyproline
<220> FEATURE:
<221> NAME/KEY: MOD_RES
```

```
<222> LOCATION: (5)..(5)
<223> OTHER INFORMATION: Norleucine
<220> FEATURE:
<221> NAME/KEY: MOD_RES
<222> LOCATION: (11)..(12)
<223> OTHER INFORMATION: D-Ala
<220> FEATURE:
<223> OTHER INFORMATION: C-term Amidation

<400> SEQUENCE: 131

Ala Ala Leu Pro Leu Pro Leu Asp Gln Thr Ala Ala
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(2)
<223> OTHER INFORMATION: D-Ala
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (6)..(6)
<223> OTHER INFORMATION: 4-hydroxyproline
<220> FEATURE:
<221> NAME/KEY: MOD_RES
<222> LOCATION: (11)..(12)
<223> OTHER INFORMATION: D-Ala
<220> FEATURE:
<223> OTHER INFORMATION: C-term Amidation

<400> SEQUENCE: 132

Ala Ala Leu Pro Leu Pro Leu Asp Gln Thr Ala Ala
1               5                   10

<210> SEQ ID NO 133
<211> LENGTH: 18
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (5)..(5)
<223> OTHER INFORMATION: Norleucine
<220> FEATURE:
<223> OTHER INFORMATION: C-term Amidation

<400> SEQUENCE: 133

Gly Gly Leu Pro Leu Pro Leu Asp Gln Thr Leu Pro Leu Asn Val Asn
1               5                   10                  15

Pro Ala

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
```

```
<220> FEATURE:
<223> OTHER INFORMATION: N-term Acetylation
<220> FEATURE:
<223> OTHER INFORMATION: C-term Amidation

<400> SEQUENCE: 134

Leu Pro Ile Pro Leu Asp Gln Thr
1               5

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (10)..(10)
<223> OTHER INFORMATION: D-Ala
<220> FEATURE:
<223> OTHER INFORMATION: C-term Amidation

<400> SEQUENCE: 135

Ala Leu Pro Leu Pro Leu Asp Gln Thr Ala
1               5                   10

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: 3,4-dehydro-L-Proline
<220> FEATURE:
<223> OTHER INFORMATION: C-term Amidation

<400> SEQUENCE: 136

Leu Pro Val Pro Leu Asp Gln Thr
1               5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 137

Val Pro Val Pro Leu Asp Gln Ser
1               5

<210> SEQ ID NO 138
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 138

Gly Gly Leu Pro Ile Pro Leu Asp Gln Thr Leu Pro Leu Asn Val Asn
1               5                   10                  15

Pro Ala

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (2)..(2)
<223> OTHER INFORMATION: 4-hydroxyproline
<220> FEATURE:
<223> OTHER INFORMATION: C-term Amidation

<400> SEQUENCE: 139

Leu Pro Ile Pro Leu Asp Gln Thr
1               5

<210> SEQ ID NO 140
<211> LENGTH: 18
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<223> OTHER INFORMATION: C-term Amidation

<400> SEQUENCE: 140

Gly Gly Leu Pro Ile Pro Leu Asp Gln Thr Leu Pro Leu Asn Val Asn
1               5                   10                  15

Pro Ala

<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(2)
<223> OTHER INFORMATION: D-Ala
<220> FEATURE:
<221> NAME/KEY: MOD_RES
<222> LOCATION: (11)..(12)
<223> OTHER INFORMATION: D-Ala
<220> FEATURE:
<223> OTHER INFORMATION: C-term Amidation

<400> SEQUENCE: 141
```

```
Ala Ala Leu Pro Leu Pro Leu Asp Gln Thr Ala Ala
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(2)
<223> OTHER INFORMATION: D-Ala
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (11)..(12)
<223> OTHER INFORMATION: D-Ala
<220> FEATURE:
<223> OTHER INFORMATION: C-term Amidation

<400> SEQUENCE: 142

Ala Ala Leu Pro Leu Pro Leu Asp Gln Thr Ala Ala
1               5                   10

<210> SEQ ID NO 143
<211> LENGTH: 18
<212> TYPE: PRT
<213> ORGANISM: Artificial Sequence
<220> FEATURE:
<223> OTHER INFORMATION: Description of Artificial Sequence: Synthetic
      ADG negative control peptide sequence
<220> FEATURE:
<223> OTHER INFORMATION: C-term Amidation

<400> SEQUENCE: 143

Ala Asp Gly Gly Leu Leu Leu Leu Asn Asn Pro Pro Pro Pro Gln Thr
1               5                   10                  15

Val Val

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      Sodium channel activity inhibiting
      peptide sequence
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (10)..(10)
<223> OTHER INFORMATION: D-Ala
<220> FEATURE:
<223> OTHER INFORMATION: C-term Amidation

<400> SEQUENCE: 144

Ala Leu Pro Ile Pro Leu Glu Gln Ser Ala
1               5                   10
```

PEPTIDE INHIBITORS OF SODIUM CHANNELS

RELATED APPLICATIONS

This application is a Continuation of U.S. patent application Ser. No. 14/878,720, filed Oct. 8, 2015, which claims the benefit of U.S. Provisional Patent Application No. 62/061,461, filed Oct. 8, 2014, the entire contents of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 102382-0042 SL.txt, 59,511 bytes in size, generated on Jul. 18, 2017 and filed via EFS-Web, is provided in lieu of a paper copy. The Sequence Listing is incorporated herein by reference into the specification for its disclosures.

FIELD OF THE INVENTION

The present invention relates to optimized peptides that are specialized non-naturally occurring peptides with improved ability to bind to sodium channels and inhibit activation of the sodium channels. The invention further relates to methods for regulating sodium absorption and fluid volume and treating disorders responsive to modulating sodium absorption by activity of sodium channels.

BACKGROUND OF THE INVENTION

Epithelial mucosal surfaces are lined with fluids whose volume and composition are precisely controlled. In the airways, a thin film of airway surface liquid helps protect mammalian airways from infection by acting as a lubricant for efficient mucus clearance (Hobbs et al., *J. Physiol.* 591: 4377 (2013), Knowles et al., *J. Clin. Invest.* 109:571 (2002)). This layer moves cephalad during mucus clearance and excess liquid that accumulates as two airways converge is eliminated by $Na^+$-modulated airway surface liquid absorption with $Na^+$ passing through the epithelial $Na^+$ channel (ENaC) (Hobbs et al., *J. Physiol.* 591: 4377 (2013), Knowles et al., *J. Clin. Invest.* 109:571 (2002)). Critically, the mechanism by which ENaC activity is regulated in the airways is poorly understood. Recently, evidence has been accumulating that molecular regulators in the airway surface liquid can serve as volume sensing signals whose dilution or concentration can alter specific cell surface receptors that control ion transport rates to either absorb or secrete airway surface liquid as needed (Chambers et al., *Respir. Physiol. Neurobiol.* 159:256 (2007)). As one of the regulated targets, ENaC must be cleaved by intracellular furin-type proteases and/or extracellular channel activating proteases (CAPs) such as prostasin to be active and to conduct $Na^+$ (Planes et al., *Curr. Top. Dev. Biol.* 78:23 (2007); Rossier, *Proc. Am. Thorac. Soc.* 1:4 (2004); Vallet et al., *Nature* 389:607 (1997); Chraibi et al., *J. Gen. Physiol.* 111:127 (1998)). ENaC can also be cleaved and activated by exogenous serine proteases such as trypsin, an action that is attenuated by the protease inhibitor aprotinin (Vallet et al., *Nature* 389:607 (1997)). When human bronchial epithelial cultures are mounted in Ussing chambers where native airway surface liquid is washed away, ENaC is predominantly active, suggesting that cell attached proteases are predominant (Bridges et al., *Am. J. Physiol. Lung Cell. Mol. Physiol.* 281:L16 (2001); Donaldson et al., *J. Biol. Chem.* 277:8338 (2002)). In contrast, under thin film conditions, where native airway surface liquid is present, ENaC activity is reduced, suggesting that airway surface liquid contains soluble protease inhibitors (Myerburg et al., *J. Biol. Chem.* 281:27942 (2006); Tarran et al., *J. Gen. Physiol.* 127:591 (2006); Gaillard et al., 2010 Pfleugers Arch, 460: 1-17).

Recently, it has been shown that the Short Palate Lung and Nasal epithelial Clone (SPLUNC1) protein comprises up to 10% of the total protein in the airway surface liquid and can readily be detected in both nasal lavage and tracheal secretions (Bingle, C. D., and Craven, C. J. (2002) PLUNC: a novel family of candidate host defense proteins expressed in the upper airways and nasopharynx *Hum Mol Genet* 11, 937; Campos, M. A., et al. (2004) Purification and characterization of PLUNC from human tracheobronchial secretions *Am J Respir Cell Mol Biol* 30, 184; Lindahl, M., Stahlbom, B., and Tagesson, C. (2001); Identification of a new potential airway irritation marker, palate lung nasal epithelial clone protein, in human nasal lavage fluid with two-dimensional electrophoresis and matrix-assisted laser desorption/ionization-time of flight *Electrophoresis* 22, 1795). SPLUNC1 appears to be a volume sensing molecule since it can be secreted onto the mucosal surface of the superficial epithelia where ENaC is expressed (Bartlett et al., *J. Leukoc. Biol.* 83:1201 (2008); Bingle et al., *J. Pathol.* 205:491 (2005)). Furthermore, SPLUNC1 has been demonstrated to contain a subdomain that functions as an inhibitor of ENaC through its N-terminal domain.

The present invention discloses novel specialized non-naturally occurring peptides that mimic the properties of SPLUNC1 in regulation of sodium channels by binding to and inhibiting ion transport to regulate sodium absorption and fluid volume and treat disorders responsive to modulating sodium absorption.

SUMMARY OF THE INVENTION

The present invention is based, in part, on the design of specialized non-naturally occurring peptides to regulate the activity of sodium channels. Accordingly, in one aspect the invention relates to a method of inhibiting the activation of a sodium channel, comprising contacting a sodium channel with a specialized non-naturally occurring peptide or a functional fragment thereof. In one embodiment, the sodium channel is an epithelial sodium channel (ENaC). In one embodiment, the specialized non-naturally occurring peptide or a functional fragment thereof binds to the sodium channel.

Another aspect of the invention relates to a method of inhibiting sodium absorption through a sodium channel, comprising contacting the sodium channel with a specialized non-naturally occurring peptide or a functional fragment thereof. In one embodiment, the specialized non-naturally occurring peptide or a functional fragment thereof binds to the sodium channel.

A further aspect of the invention relates to a method of increasing the volume of fluid lining an epithelial mucosal surface, comprising contacting a sodium channel present on the epithelial mucosal surface with a specialized non-naturally occurring peptide or a functional fragment thereof. In one embodiment, the specialized non-naturally occurring peptide or a functional fragment thereof binds to the sodium channel.

Another aspect of the invention relates to a method of reducing the level of a sodium channel present on the surface of a cell, comprising contacting the sodium channel with a specialized non-naturally occurring peptide or a functional fragment thereof. In one embodiment, the specialized non-naturally occurring peptide or a functional fragment thereof binds to the sodium channel.

A further aspect of the invention relates to a method of treating a disorder responsive to inhibition of sodium absorption across an epithelial mucosal surface in a subject in need thereof, comprising delivering to the subject a therapeutically effective amount of a specialized non-naturally occurring peptide or a functional fragment thereof. In one embodiment, the specialized non-naturally occurring peptide or a functional fragment thereof binds to the sodium channel.

Another aspect of the invention relates to a method of regulating salt balance, blood volume, and/or blood pressure in a subject in need thereof, comprising delivering to the subject a therapeutically effective amount of a specialized non-naturally occurring peptide or a functional fragment thereof. In one embodiment, the specialized non-naturally occurring peptide or a functional fragment thereof binds to the sodium channel.

Another aspect of the invention relates to a specialized non-naturally occurring peptide or a functional fragment thereof that mimics the sodium channel binding domain of a PLUNC protein and binds to a sodium channel, wherein cleavage of the sodium channel by a protease is inhibited when bound to the peptide.

Another aspect of the invention relates to a kit comprising the peptide of the invention.

Another aspect of the invention relates to the use of a specialized non-naturally occurring peptide or a functional fragment thereof for the preparation of a medicament to treat a disorder responsive to inhibition of sodium absorption in a subject in need thereof.

These and other aspects of the invention are set forth in more detail in the description of the invention below.

BRIEF DESCRIPTION OF THE DRAWINGS

FIG. 6 shows the results of an experiment analyzing the effects of various peptides on internalization of alpha-ENaC in HEK293T cells when GFP-tagged alpha-ENaC is co-expressed only with gamma ENaC and no beta-ENaC. In this figure, SEQ ID NO:143 (negative control peptide) and water (vehicle) controls are used along with S18 (SEQ ID NO:1) and SEQ ID NO:128. While SEQ ID NO:1 AND SEQ ID NO:128 are effective in reducing alpha-ENaC when beta-ENaC is co-expressed, no effect is observed in this experiment when beta-ENaC is not present.

DETAILED DESCRIPTION OF THE INVENTION

Figure 1:
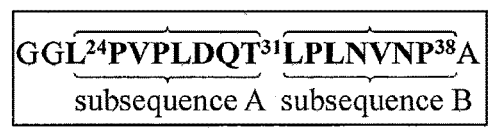
FIG. 1 shows the sequence of S18 (SEQ ID NO:1). Highlighted in red are residues essential for ENaC interaction, while highlighted in blue are residues that were found not to contribute.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "consists essentially of" (and grammatical variants), as applied to a peptide sequence of this invention, means a peptide that consists of both the recited sequence (e.g., SEQ ID NO) and a total of ten or less (e.g., 1, 2, 3, 4, 5, 6, 7, 8, 9, or 10) additional amino acids on the N-terminal and/or C-terminal ends of the recited sequence such that the function of the peptide is not materially altered. The total of ten or less additional amino acids includes the total number of additional amino acids on both ends added together. The term "materially altered," as applied to peptides of the invention, refers to an increase or decrease in binding activity (e.g., to a sodium channel or specialized non-naturally occurring peptide) of at least about 50% or more as compared to the activity of a peptide consisting of the recited sequence.

The term "modulate," "modulates," or "modulation" refers to enhancement (e.g., an increase) or inhibition (e.g., a decrease) in the specified level or activity.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, or even fifteen-fold.

The term "inhibit" or "reduce" or grammatical variations thereof as used herein refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectible activity (at most, an insignificant amount, e.g., less than about 10% or even 5%).

The term "contact" or grammatical variations thereof as used with respect to a specialized non-naturally occurring peptide and a sodium channel, refers to bringing the specialized non-naturally occurring peptide and the sodium channel in sufficiently close proximity to each other for one to exert a biological effect on the other. In some embodiments, the term contact means binding of the specialized non-naturally occurring peptide to the sodium channel.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

By the terms "treat," "treating," or "treatment of," it is intended that the severity of the subject's condition is reduced or at least partially improved or modified and that some alleviation, mitigation or decrease in at least one clinical symptom is achieved.

The term "fragment," as applied to a peptide, will be understood to mean an amino acid sequence of reduced length relative to a reference peptide or amino acid sequence and comprising, consisting essentially of, and/or consisting of an amino acid sequence of contiguous amino acids identical to the reference peptide or amino acid sequence. Such a peptide fragment according to the invention may be, where appropriate, included in a larger polypeptide of which it is a constituent. In some embodiments, such fragments can comprise, consist essentially of, and/or consist of peptides having a length of at least about 4, 5, 6, 7, 8, 9, 10, or more consecutive amino acids of a peptide or amino acid sequence according to the invention. In other embodiments, such fragments can comprise, consist essentially of, and/or consist of peptides having a length of less than about 10, 9, 8, 7, 6, 5, 4, or less consecutive amino acids of a peptide or amino acid sequence according to the invention.

As used herein, the terms "protein" and "polypeptide" are used interchangeably and encompass both peptides and proteins, unless indicated otherwise.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a peptide of the invention (or a fragment thereof) to all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

As used herein, a "functional" peptide or "functional fragment" is one that substantially retains at least one biological activity normally associated with that peptide (e.g., binding to or inhibiting a sodium channel). In particular embodiments, the "functional" peptide or "functional fragment" substantially retains all of the activities possessed by the unmodified peptide. By "substantially retains" biological activity, it is meant that the peptide retains at least about 20%, 30%, 40%, 50%, 60%, 75%, 85%, 90%, 95%, 97%, 98%, 99%, or more, of the biological activity of the native polypeptide (and can even have a higher level of activity than the native peptide). A "non-functional" peptide is one that exhibits little or essentially no detectable biological activity normally associated with the peptide (e.g., at most, only an insignificant amount, e.g., less than about 10% or even 5%). Biological activities such as protein binding and sodium channel inhibitory activity can be measured using assays that are well known in the art and as described herein.

The term "about," as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even ±0.1% of the specified amount.

A first aspect of the invention relates to the ability of specialized non-naturally occurring peptides to bind to a sodium channel and prevent activation of the sodium channel, thereby inhibiting the flow of sodium ions. Thus, one aspect of the present invention relates to a method of inhibiting the activation of a sodium channel, comprising contacting (e.g., binding) a sodium channel with a specialized non-naturally occurring peptide or a functional fragment thereof. In one embodiment, the sodium channel is an epithelial sodium channel (ENaC), e.g., human ENaC, or a non-human mammalian ENaC. In another embodiment, the sodium channel is one that is similar in sequence and/or structure to ENaC, such as acid-sensing ion channels (ASIC). The inhibition of sodium channel activation can be measured by any method known in the art or disclosed herein, including, without limitation, measuring sodium flow or change in potential across a membrane, across a cell, or across a natural or artificial lining. The inhibition can be at least about 20%, e.g., at least about 30%, 40%, 50%, 60%, 70%, 80%, 90%, or 100%.

The method of inhibiting the activation of a sodium channel can be carried out, e.g., on an isolated sodium channel, a sodium channel in an artificial membrane, or a sodium channel in a cell. In one embodiment, the sodium channel is present in an isolated cell, e.g., a cultured primary cell or cell line. In another embodiment, the isolated cell is part of an epithelial cell culture, e.g., a natural or artificial epithelial lining, e.g., a cell culture in a device (such as an Ussing chamber) in which characteristics such as ion flow and/or potential can be measured across lining. In another embodiment, the cell is part of an isolated tissue or a tissue culture. In a further embodiment, the cell can be present in an animal, e g, an animal that is a disease model or a subject in need of treatment.

In one embodiment, the step of contacting (e.g., binding) the sodium channel with a specialized non-naturally occurring peptide comprises delivering the specialized non-naturally occurring peptide or a functional fragment or homolog thereof to a cell comprising the sodium channel.

As used herein, the term "homolog" is used to refer to a polypeptide which differs from a the disclosed specialized non-naturally occurring peptide by modifications to the specialized non-naturally occurring peptide, but which significantly retains a biological activity of the disclosed non-naturally occurring peptide. Minor modifications include, without limitation, changes in one or a few amino acid side chains, changes to one or a few amino acids (including deletions, insertions, and substitutions), changes in stereochemistry of one or a few atoms, and minor derivatizations, including, without limitation, methylation, glycosylation, phosphorylation, acetylation, myristoylation, prenylation, palmitoylation, amidation, and addition of glycosylphosphatidyl inositol. The term "substantially retains," as used herein, refers to a fragment, homolog, or other variant of a peptide that retains at least about 20% of the activity of the naturally occurring peptide (e.g., binding to a sodium channel), e.g., about 30%, 40%, 50% or more. Other biological activities, depending on the peptide, may include enzyme activity, receptor binding, ligand binding, induction of a growth factor, a cell signal transduction event, etc.

In one embodiment, the method comprises delivering to a cell comprising a sodium channel an isolated specialized non-naturally occurring peptide. In exemplary embodiments, the specialized non-naturally occurring peptide comprises, consists essentially of, or consists of the disclosed specialized non-naturally occurring peptide or a functional fragment thereof. In another embodiment, the isolated specialized non-naturally occurring peptide comprises, consists essentially of, or consists of an amino acid sequence that is at least 70% identical, e.g., at least 75%, 80%, 85%, 90%, 95%, 96%, 97%, 98%, or 99% identical to the publicly known amino acid sequence or a functional fragment thereof. In some embodiments, the peptides comprise a portion of the natural amino acid sequence of a PLUNC protein with one or more conservative substitutions with natural or non-natural amino acids and/or one or more additions of non-natural amino acids. Conservative substitutions are described below. In some embodiments, the peptides comprise one or more terminal modifications as described below.

Non-limiting examples of peptides of the invention are disclosed in Table 1 below. In some embodiments, the peptides of the invention may comprise one or more additional residues at the amino- and/or carboxyl-terminal ends. In some embodiments, the one or more additional residues are D-alanines. For example, a peptide may comprise one or two D-alanines at the amino- and/or carboxyl-terminal ends.

The specialized non-naturally occurring peptides of the invention also include functional portions or fragments. The length of the fragment is not critical as long as it substantially retains the biological activity of the peptide (e.g., sodium channel binding activity). Illustrative fragments comprise at least about 4, 5, 6, 7, 8, 9, 10, or more contiguous amino acids of a specialized non-naturally occurring peptide. In other embodiments, the fragment comprises no more than about 10, 9, 8, 7, 6, 5, or 4 contiguous amino acids of a specialized non-naturally occurring peptide.

Likewise, those skilled in the art will appreciate that the present invention also encompasses fusion polypeptides comprising a specialized non-naturally occurring peptides peptide or a functional fragment thereof. As another alternative, the fusion protein can comprise a reporter molecule. In other embodiments, the fusion protein can comprise a polypeptide that provides a function or activity that is the same as or different from the activity of the peptide, e.g., a targeting, binding, or enzymatic activity or function.

Likewise, it will be understood that the peptides specifically disclosed herein will typically tolerate substitutions in the amino acid sequence and substantially retain biological activity. To identify peptides of the invention other than those specifically disclosed herein, amino acid substitutions may be based on any characteristic known in the art, including the relative similarity or differences of the amino acid side-chain substituents, for example, their hydrophobicity, hydrophilicity, charge, size, and the like.

TABLE 1

| SEQ ID No | term | | | | | | | | | | | | | | | | |
|---|---|---|---|---|---|---|---|---|---|---|---|---|---|---|---|---|---|
| 1 | NH3 | G | G | L | P | V | P | L | D | Q | T | L | P | L | N | V | N | P | A | 2 |
| 138 | NH3 | G | G | L | P | I | P | L | D | Q | T | L | P | L | N | V | N | P | A | 2 |
| 119 | NH3 | | | L | P | V | P | L | D | Q | T | L | P | L | N | V | N | P | | 2 |
| 120 | NH3 | | | L | P | V | P | L | D | Q | T | | | 2 |
| 121 | NH3 | | | Nle | P | V | P | L | D | Q | T | | | 2 |
| 122 | NH3 | | | L | P | Nle | P | L | D | Q | T | | | 2 |
| 142 | NH3 | a | a | L | P | Nle | P | L | D | Q | T | a | a | 2 |

TABLE 1-continued

| SEQ ID No | term | | | | | | | | | | | |
|---|---|---|---|---|---|---|---|---|---|---|---|---|
| 135 | NH3 | | a | L | P | Nle | P | L | D | Q | T | a | 2 |
| 123 | NH3 | | | L | P | V | P | Nle | D | Q | T | | 2 |
| 124 | NH3 | | | L | P | V | P | L | D | N | T | | 2 |
| 125 | NH3 | | | L | P | V | P | L | E | Q | T | | 2 |
| 126 | NH3 | | | L | P | V | P | L | D | Q | S | | 2 |
| 127 | NH3 | | | L | P | I | P | L | D | Q | T | | 2 |
| 128 | NH3 | a | a | L | P | I | P | L | D | Q | T | a | a | 2 |
| 134 | Ac | | | L | P | I | P | L | D | Q | T | | 2 |
| 10 | Ac | | | L | P | V | P | L | D | Q | T | | 2 |
| 11 | Ac | | | L | DHP | V | P | L | D | Q | T | | 2 |
| 136 | NH3 | | | L | DHP | V | P | L | D | Q | T | | 2 |
| 12 | NH3 | | | L | P | V | DHP | L | D | Q | T | | 2 |
| 13 | NH3 | | | L | DHP | V | DHP | L | D | Q | T | | 2 |
| 14 | NH3 | | | L | 2PP | V | P | L | D | Q | T | | 2 |
| 15 | NH3 | | | L | P | V | 2PP | L | D | Q | T | | 2 |
| 16 | NH3 | | | L | HYP | V | P | L | D | Q | T | | 2 |
| 17 | NH3 | | | L | P | V | HYP | L | D | Q | T | | 2 |
| 18 | NH3 | | | L | HYP | V | HYP | L | D | Q | T | | 2 |
| 19 | NH3 | | | L | P | V | P | L | E | Q | S | | 2 |
| 20 | NH3 | | | L | P | V | P | L | E | Q | MS | | 2 |
| 21 | NH3 | | | L | P | V | P | V | D | Q | T | | 2 |
| 22 | NH3 | | | L | P | V | P | V | E | Q | S | | 2 |
| 23 | NH3 | | | L | P | V | P | V | D | Q | S | | 2 |
| 24 | NH3 | | | V | P | V | P | L | D | Q | T | | 2 |
| 25 | NH3 | | | L | P | L | P | L | D | Q | S | | 2 |
| 26 | NH3 | | | V | P | L | P | L | D | Q | S | | 2 |
| 27 | NH3 | | | L | P | L | P | L | D | Q | T | | 2 |
| 141 | NH3 | a | a | L | P | L | P | L | D | Q | T | a | a | 2 |
| 28 | NH3 | | | V | HYP | L | HYP | V | E | Q | S | | 2 |
| 29 | NH3 | | | V | P | L | P | V | E | Q | S | | 2 |
| 30 | NH3 | | | L | P | L | P | L | E | Q | S | | 2 |
| 31 | NH3 | | | L | P | mV | P | L | D | Q | S | | 2 |
| 32 | NH3 | | | L | P | Nle | P | L | D | Q | T | | 2 |
| 33 | NH3 | | | L | P | Nle | P | V | E | Q | S | | 2 |
| 34 | NH3 | | | L | P | Nle | P | V | E | Q | S | | 2 |
| 35 | NH3 | | | L | HYP | Nle | HYP | L | E | Q | S | | 2 |
| 36 | NH3 | | | L | HYP | Nle | HYP | V | E | Q | S | | 2 |
| 37 | Ac | | | L | P | V | DHP | L | D | Q | T | | 2 |

TABLE 1-continued

| SEQ ID No | term | | | | | | | | |
|---|---|---|---|---|---|---|---|---|---|
| 38 | Ac | L | DHP | V | DHP | L | D | Q | T | 2 |
| 39 | Ac | L | 2PP | V | P | L | D | Q | T | 2 |
| 40 | Ac | L | P | V | 2PP | L | D | Q | T | 2 |
| 41 | Ac | L | HYP | V | P | L | D | Q | T | 2 |
| 42 | Ac | L | P | V | HYP | L | D | Q | T | 2 |
| 43 | Ac | L | HYP | V | HYP | L | D | Q | T | 2 |
| 44 | Ac | L | P | V | P | L | E | Q | S | 2 |
| 45 | Ac | L | P | V | P | L | E | Q | MS | 2 |
| 46 | Ac | L | P | V | P | V | D | Q | T | 2 |
| 47 | Ac | L | P | V | P | V | E | Q | S | 2 |
| 48 | Ac | L | P | V | P | V | D | Q | S | 2 |
| 49 | Ac | V | P | V | P | L | D | Q | T | 2 |
| 50 | Ac | L | P | L | P | L | D | Q | S | 2 |
| 51 | Ac | V | P | L | P | L | D | Q | S | 2 |
| 52 | Ac | L | P | L | P | L | D | Q | T | 2 |
| 53 | Ac | V | HYP | L | HYP | V | E | Q | S | 2 |
| 54 | Ac | V | P | L | P | V | E | Q | S | 2 |
| 55 | Ac | L | P | L | P | L | E | Q | S | 2 |
| 56 | Ac | L | P | mV | P | L | D | Q | S | 2 |
| 57 | Ac | L | P | Nle | P | L | D | Q | T | 2 |
| 58 | Ac | L | P | Nle | P | V | E | Q | S | 2 |
| 59 | Ac | L | P | Nle | P | V | E | Q | S | 2 |
| 60 | Ac | L | HYP | Nle | HYP | L | E | Q | S | 2 |
| 61 | Ac | L | HYP | Nle | HYP | V | E | Q | S | 2 |
| 62 | Ac | L | DHP | V | P | L | D | Q | T | 2 |
| 63 | NH3 | L | P | V | DHP | L | D | Q | T | 2 |
| 64 | NH3 | L | DHP | V | DHP | L | D | Q | T | 2 |
| 65 | NH3 | L | 2PP | V | P | L | D | Q | T | 2 |
| 66 | NH3 | L | P | V | 2PP | L | D | Q | T | 2 |
| 67 | NH3 | L | HYP | V | P | L | D | Q | T | 2 |
| 68 | NH3 | L | P | V | HYP | L | D | Q | T | 2 |
| 69 | NH3 | L | HYP | V | HYP | L | D | Q | T | 2 |
| 70 | NH3 | L | P | V | P | L | E | Q | S | 2 |
| 71 | NH3 | L | P | V | P | L | E | Q | MS | 2 |
| 72 | NH3 | L | P | V | P | V | D | Q | T | 2 |
| 73 | NH3 | L | P | V | P | V | E | Q | S | 2 |
| 74 | NH3 | L | P | V | P | V | D | Q | S | 2 |
| 75 | NH3 | V | P | V | P | L | D | Q | T | 2 |

TABLE 1-continued

| SEQ ID No | term | | | | | | | | |
|---|---|---|---|---|---|---|---|---|---|
| 137 | NH3 | V | P | V | P | L | D | Q | S | 2 |
| 76 | NH3 | L | P | L | P | L | D | Q | S | 2 |
| 77 | NH3 | V | P | L | P | L | D | Q | S | 2 |
| 78 | NH3 | L | P | L | P | L | D | Q | T | 2 |
| 79 | NH3 | V | HYP | L | HYP | V | E | Q | S | 2 |
| 80 | NH3 | V | P | L | P | V | E | Q | S | 2 |
| 81 | NH3 | L | P | L | P | L | E | Q | S | 2 |
| 82 | NH3 | L | P | mV | P | L | D | Q | S | 2 |
| 83 | NH3 | L | P | Nle | P | L | D | Q | T | 2 |
| 84 | NH3 | L | P | Nle | P | V | E | Q | S | 2 |
| 85 | NH3 | L | P | Nle | P | V | E | Q | S | 2 |
| 86 | NH3 | L | HYP | Nle | HYP | L | E | Q | S | 2 |
| 87 | NH3 | L | HYP | Nle | HYP | V | E | Q | S | 2 |
| 88 | Ac | L | P | V | DHP | L | D | Q | T | 2 |
| 89 | Ac | L | DHP | V | DHP | L | D | Q | T | 2 |
| 90 | Ac | L | 2PP | V | P | L | D | Q | T | 2 |
| 91 | Ac | L | P | V | 2PP | L | D | Q | T | 2 |
| 92 | Ac | L | HYP | V | P | L | D | Q | T | 2 |
| 93 | Ac | L | P | V | HYP | L | D | Q | T | 2 |
| 94 | Ac | L | HYP | V | HYP | L | D | Q | T | 2 |
| 95 | Ac | L | P | V | P | L | E | Q | S | 2 |
| 96 | Ac | L | P | V | P | L | E | Q | MS | 2 |
| 97 | Ac | L | P | V | P | V | D | Q | T | 2 |
| 98 | Ac | L | P | V | P | V | E | Q | S | 2 |
| 99 | Ac | L | P | V | P | V | D | Q | S | 2 |
| 100 | Ac | V | P | V | P | L | D | Q | T | 2 |
| 101 | Ac | L | P | L | P | L | D | Q | S | 2 |
| 102 | Ac | V | P | L | P | L | D | Q | S | 2 |
| 103 | Ac | L | P | L | P | L | D | Q | T | 2 |
| 104 | Ac | V | HYP | L | HYP | V | E | Q | S | 2 |
| 105 | Ac | V | P | L | P | V | E | Q | S | 2 |
| 106 | Ac | L | P | L | P | L | E | Q | S | 2 |
| 107 | Ac | L | P | mV | P | L | D | Q | S | 2 |
| 108 | Ac | L | P | Nle | P | L | D | Q | T | 2 |
| 109 | Ac | L | P | Nle | P | V | E | Q | S | 2 |
| 110 | Ac | L | P | Nle | P | V | E | Q | S | 2 |
| 111 | Ac | L | HYP | Nle | HYP | L | E | Q | S | 2 |
| 112 | Ac | L | HYP | Nle | HYP | V | E | Q | S | 2 |

TABLE 1-continued

| SEQ ID No | term | | | | | | | | | | | | | | | | | | | |
|---|---|---|---|---|---|---|---|---|---|---|---|---|---|---|---|---|---|---|---|---|
| 113 | NH3 | | | L | P | V | P | L | D | Q | T | | | | | | | | | 2 |
| 114 | NH3 | | | | | | | | D | Q | T | L | P | L | N | V | N | P | | 2 |
| 115 | NH3 | | | L | P | V | P | L | D | Q | T | L | P | L | | | | | | 2 |
| 129 | NH3 | | | L | P | Ahp | P | L | D | Q | T | | | | | | | | | 2 |
| 130 | NH3 | | | L | P | F | P | L | D | Q | T | | | | | | | | | 2 |
| 131 | NH3 | a | a | L | HYP | Nle | P | L | D | Q | T | a | a | | | | | | | 2 |
| 132 | NH3 | a | a | L | P | Nle | HYP | L | D | Q | T | a | a | | | | | | | 2 |
| 133 | NH3 | G | G | L | P | Nle | P | L | D | Q | T | L | P | L | N | V | N | P | A | 2 |
| 139 | NH3 | | | L | HYP | I | P | L | D | Q | T | | | | | | | | | 2 |
| 140 | NH3 | G | G | L | P | I | P | L | D | Q | T | L | P | L | N | V | N | P | A | 2 |
| 144 | NH3 | | a | L | P | I | P | L | E | Q | S | a | | | | | | | | 2 |

Where
a = D-alanine,
Nle = Norleucine,
HYP = 4-hydroxyproline,
DHP = 3,4-dehydro-L-proline,
Ahp = aminoheptanoic acid,
2PP = (2R,5S)-5-phenyl-pyrrolidine-2-carboxylic acid,
MS = L-α-methylserine, and
mV = N-methylvaline In identifying amino acid sequences encoding peptides other than those specifically disclosed herein, the hydropathic index of amino acids may be considered. The importance of the hydropathic amino acid index in conferring interactive biologic function on a protein is generally understood in the art (see, Kyte and Doolittle, *J. Mol. Biol.* 157:105 (1982); incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, id.), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Accordingly, the hydropathic index of the amino acid (or amino acid sequence) may be considered when modifying the peptides specifically disclosed herein.

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±I); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Thus, the hydrophilicity of the amino acid (or amino acid sequence) may be considered when identifying additional peptides beyond those specifically disclosed herein.

Peptides (and fragments thereof) of the invention include peptides that have at least about 70%, 80%, 85%, 90%, 95%, 96%, 97%, 98%, 99% or higher amino acid sequence identity with the peptide sequences disclosed herein.

As is known in the art, a number of different programs can be used to identify whether a polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.,* 266:460 (1996); blast.mustl/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment may include the introduction of gaps in the sequences to be aligned. In addition, for sequences which contain either more or fewer amino acids than the peptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Peptides and fragments of the invention can be modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by any suitable methods. For example, one or more non-naturally occurring amino acids, such as D-alanine, can be added to the termini. Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Additionally, the peptide terminus can be modified, e.g., by acetylation of the N-terminus and/or amidation of the C-terminus. Likewise, the peptides can be covalently or noncovalently coupled to pharmaceutically acceptable "carrier" proteins prior to administration.

In one embodiment, the peptides or fragments thereof of the invention are administered directly to a subject. Generally, the compounds of the invention will be suspended in a pharmaceutically-acceptable carrier (e.g., physiological saline) and administered orally or by intravenous infusion, or administered subcutaneously, intramuscularly, intrathecally, intraperitoneally, intrarectally, intravaginally, intranasally, intragastrically, intratracheally, or intrapulmonarily. In another embodiment, the intratracheal or intrapulmonary delivery can be accomplished using a standard nebulizer, jet nebulizer, wire mesh nebulizer, dry powder inhaler, or metered dose inhaler. They can be delivered directly to the site of the disease or disorder, such as lungs, kidney, or intestines. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100.0 µg/kg. Wide variations in the needed dosage are to be expected in view of the variety of peptides, fragments, and homologs available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-, 3-, 4-, 6-, 8-, 10-; 20-, 50-, 100-, 150-, or more fold). Encapsulation of the peptides, fragments, and homologs in a suitable delivery vehicle (e.g., polymeric microparticles or implantable devices) may increase the efficiency of delivery, particularly for oral delivery.

According to certain embodiments, the peptides, or fragments thereof can be targeted to specific cells or tissues in vivo. Targeting delivery vehicles, including liposomes and targeted systems are known in the art. For example, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., *Biochemistry* 25:5500 (1986); Ho et al., *J. Biol. Chem.* 262:13979 (1987); Ho et al., *J. Biol. Chem.* 262:13973 (1987); and U.S. Pat. No. 4,957,735 to Huang et al., each of which is incorporated herein by reference in its entirety).

Another aspect of the invention relates to a method of inhibiting sodium absorption through a sodium channel, comprising contacting (e.g., binding) the sodium channel with a specialized non-naturally occurring peptide or fragment thereof. Inhibition of sodium absorption can be measured by any technique known in the art or disclosed herein.

Another aspect of the invention relates to a method of increasing the volume of fluid lining an epithelial mucosal surface, comprising contacting (e.g., binding) a sodium channel present on the epithelial mucosal surface with a specialized non-naturally occurring peptide or a functional fragment or homolog thereof. The volume of fluid lining an epithelial mucosal surface can be measured by any technique known in the art or disclosed herein.

A further aspect of the invention relates to a method of reducing the level of a sodium channel present on the surface of a cell, comprising contacting (e.g., binding) the sodium channel with a specialized non-naturally occurring peptide or a functional fragment or homolog thereof.

An additional aspect of the invention relates to a method of treating a disorder responsive to inhibition of sodium absorption across an epithelial mucosal surface in a subject in need thereof, comprising delivering to the subject a therapeutically effective amount of a specialized non-naturally occurring peptide or a functional fragment or homolog thereof. In one embodiment, the invention encompasses a method for treating a symptom of a disorder responsive to inhibition of sodium absorption across an epithelial mucosal surface in a subject in need thereof, comprising administering a peptide comprising a sequence selected from SEQ ID NOS:2-128 to the subject. The disorder in the methods of the invention can be, in non-limiting examples, a lung disorder (e.g., cystic fibrosis, non-cystic fibrosis bronchiectasis, chronic obstructive pulmonary disease, acute or chronic bronchitis, or asthma), a gastrointestinal disorder (e.g., inflammatory bowel disease), a kidney disorder, or a cardiovascular disorder.

Another aspect of the invention relates to a method of regulating salt balance, blood volume, and/or blood pressure in a subject in need thereof, comprising delivering to the subject a therapeutically effective amount of a specialized non-naturally occurring peptide or a functional fragment or homolog thereof.

A third aspect of the invention relates to products that can be used to carry out the methods disclosed herein. Thus, one aspect of the invention relates to a peptide comprising the sequence:

$$X_1-X_2-X_3-X_4-X_5-X_6-X_7-X_8 \quad \text{(SEQ ID NO: 116)}$$

wherein:
$X_1$ is leucine or a conservative substitution with a natural or non-natural amino acid;
$X_2$ is proline or a conservative substitution with a natural or non-natural amino acid;
$X_3$ is valine or a conservative substitution with a natural or non-natural amino acid;
$X_4$ is proline or a conservative substitution with a natural or non-natural amino acid;
$X_5$ is leucine or a conservative substitution with a natural or non-natural amino acid;
$X_6$ is aspartic acid or a conservative substitution with a natural or non-natural amino acid;
$X_7$ is glutamine or a conservative substitution with a natural or non-natural amino acid; and
$X_8$ is threonine or a conservative substitution with a natural or non-natural amino acid;
or a functional fragment thereof.

Another aspect of the invention relates to a peptide comprising the sequence:

$$X_1-X_2-X_3-X_4-X5-X_6-X_7-X_8 \quad \text{(SEQ ID NO: 117)}$$

wherein:
$X_1$ is leucine, norleucine, or valine;
$X_2$ is proline, 4-hydroxyproline, (2R,5S)-5-phenyl-pyrrolidine-2-carboxylic acid, or 3,4-dehydro-L-proline;
$X_3$ is valine, leucine, norleucine, or N-methylvaline;
$X_4$ is proline, 4-hydroxyproline, (2R,5S)-5-phenyl-pyrrolidine-2-carboxylic acid, or 3,4-dehydro-L-proline;
$X_5$ is leucine, norleucine, or valine;
$X_6$ is aspartic acid or glutamic acid;
$X_7$ is glutamine or asparagine; and
$X_8$ is threonine, serine, or L-α-methylserine; or a functional fragment thereof.

A further aspect of the invention relates to a peptide comprising the sequence:

$$X_1-X_2-X_3-X_4-X_5-X_6-X_7-X_8-X_9-X_{10}-X_{11}-X_{12}-X_{13}-X_{14}-X_{15} \quad \text{(SEQ ID NO: 118)}$$

wherein: $X_1$ is leucine or a conservative substitution with a natural or non-natural amino acid;
$X_2$ is proline or a conservative substitution with a natural or non-natural amino acid;
$X_3$ is valine or a conservative substitution with a natural or non-natural amino acid;
$X_4$ is proline or a conservative substitution with a natural or non-natural amino acid;
$X_5$ is leucine or a conservative substitution with a natural or non-natural amino acid;
$X_6$ is aspartic acid or a conservative substitution with a natural or non-natural amino acid;
$X_7$ is glutamine or a conservative substitution with a natural or non-natural amino acid;
$X_8$ is threonine or a conservative substitution with a natural or non-natural amino acid;
$X_9$ is threonine or a conservative substitution with a natural or non-natural amino acid;
$X_{10}$ is leucine or a conservative substitution with a natural or non-natural amino acid;
$X_{11}$ is proline or a conservative substitution with a natural or non-natural amino acid;
$X_{12}$ is asparagine or a conservative substitution with a natural or non-natural amino acid;
$X_{13}$ is valine or a conservative substitution with a natural or non-natural amino acid;
$X_{14}$ is asparagine or a conservative substitution with a natural or non-natural amino acid;
$X_{15}$ is proline or a conservative substitution with a natural or non-natural amino acid; or a functional fragment thereof.

In some embodiments, the peptide comprises a sequence selected from the group consisting of SEQ ID NOS:4-142 and SEQ ID NO:144. In one embodiment, the peptide comprises the sequence of SEQ ID NO:5 or SEQ ID NO:122. In one embodiment, the peptide comprises the sequence of SEQ ID NO:2 (aaLPVPLDQTLPLNVNPaa) or SEQ ID NO:119. In one embodiment, the peptide comprises the sequence of SEQ ID NO:127 or SEQ ID NO:128 (aaLPIPLDQTaa).

In certain embodiments, the peptides of the invention comprise at least one modified terminus, e.g., to protect the peptide against degradation. In some embodiments, the N-terminus is acetylated and/or the C-terminus is amidated. In some embodiments, the peptide comprises the sequence of any one of SEQ ID NOS:10-127, 129, 130, 133, 134, or 136-140, further comprising one or two D-alanines at the amino- and/or carboxyl-terminal ends.

In certain embodiments, the peptides of the invention comprise at least one non-natural amino acid (e.g., 1, 2, 3, or more) or at least one terminal modification (e.g., 1 or 2). In some embodiments, the peptide comprises at least one non-natural amino acid and at least one terminal modification.

In certain embodiments, the peptide mimics the sodium channel binding domain of a PLUNC protein. The sodium channel binding domain is the minimal fragment of the PLUNC protein required to have substantially the same binding activity to the sodium channel as the full length PLUNC protein. The term "substantially the same binding activity" refers to an activity that is at least about 50% of the binding activity of the full length protein, e.g., at least about 60%, 70%, 80%, or 90% of the binding activity. In some embodiments, the peptide has at least the same binding activity as the full length PLUNC protein. In one embodiment, the sodium channel is ENaC, e.g., human ENaC. In another embodiment, the sodium channel is one that is similar in sequence and/or structure to ENaC, such as acid-sensing ion channels (ASIC).

The peptides of the present invention can optionally be delivered in conjunction with other therapeutic agents. The additional therapeutic agents can be delivered concurrently with the peptides of the invention. As used herein, the word "concurrently" means sufficiently close in time to produce a combined effect (that is, concurrently can be simultaneously, or it can be two or more events occurring within a short time period before or after each other). In one embodiment of the invention, the specialized non-naturally occurring peptide is delivered to a patient concurrently with a compound that modulates the function of the Cystic fibrosis transmembrane conductance regulator (CFTR) where the combined activity of the specialized non-naturally occurring peptide and the CFTR-targeted agent have superior activity to the CFTR-targeted agent alone. In another embodiment of the invention, the specialized non-naturally occurring peptide is delivered to a patient concurrently with a mucolytic compound where the combined activity of the specialized non-naturally occurring peptide and the mucolytic agent have superior activity to the mucolytic agent alone. In yet another embodiment of the invention, the specialized non-naturally occurring peptide is delivered to a patient concurrently with a long acting B-agonist compound (LABA) where the combined activity of the specialized non-naturally occurring peptide and the LABA agent have superior activity to the LABA alone. In yet another embodiment of the invention, the specialized non-naturally occurring peptide is delivered to a patient concurrently with a glucocorticoid agonist where the combined activity of the specialized non-naturally occurring peptide and the glucocorticoid agent have superior activity to the glucocorticoid alone.

Another aspect of the invention relates to a kit comprising the peptide of the invention and useful for carrying out the methods of the invention. The kit may further comprise additional reagents for carrying out the methods (e.g., buffers, containers, additional therapeutic agents) as well as instructions.

As a further aspect, the invention provides pharmaceutical formulations and methods of administering the same to achieve any of the therapeutic effects (e.g., modulation of sodium absorption) discussed above. The pharmaceutical formulation may comprise any of the reagents discussed above in a pharmaceutically acceptable carrier, e.g., a specialized non-naturally occurring peptide or functional fragment thereof.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The peptides of the invention can be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the peptide (including the physiologically acceptable salts thereof) is typically admixed with, inter alia, an acceptable carrier. The carrier can be a solid or a liquid, or both, and is preferably formulated with the peptide as a unit-dose formulation, for example, a tablet, which can contain from 0.01 or 0.5% to 95% or 99% by weight of the peptide. One or more peptides can be incorporated in the formulations of the invention, which can be prepared by any of the well-known techniques of pharmacy.

A further aspect of the invention is a method of treating subjects in vivo, comprising administering to a subject a pharmaceutical composition comprising a peptide of the invention in a pharmaceutically acceptable carrier, wherein the pharmaceutical composition is administered in a therapeutically effective amount. Administration of the peptides of the present invention to a human subject or an animal in need thereof can be by any means known in the art for administering compounds.

The formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, into the pancreas, or into a tumor or the tissue surrounding a tumor). The most suitable route in any given case will depend on the nature and severity of the condition being treated and on the nature of the particular peptide which is being used.

For injection, the carrier will typically be a liquid, such as sterile pyrogen-free water, sterile normal saline, hypertonic saline, pyrogen-free phosphate-buffered saline solution, bacteriostatic water, or Cremophor EL[R] (BASF, Parsippany, N.J.). For other methods of administration, the carrier can be either solid or liquid.

For oral administration, the peptide can be administered in solid dosage forms, such as capsules, tablets, and powders, or in liquid dosage forms, such as elixirs, syrups, and suspensions. Peptides can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the compound in a flavored base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the peptide, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising a peptide of the invention, in a unit dosage form in a sealed container. The peptide or salt is provided in the form of a lyophilizate which is capable of being reconstituted with a suitable pharmaceutically acceptable carrier to form a liquid composition suitable for injection thereof into a subject. The unit dosage form typically comprises from about 1 mg to about 10 grams of the peptide or salt. When the peptide or salt is substantially water-insoluble, a sufficient amount of emulsifying agent which is pharmaceutically acceptable can be employed in sufficient quantity to emulsify the peptide or salt in an aqueous carrier. One such useful emulsifying agent is phosphatidyl choline.

Formulations suitable for rectal administration are preferably presented as unit dose suppositories. These can be prepared by admixing the peptide with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the peptides. Suitable formulations comprise citrate or bis/tris buffer (pH 6) or ethanol/water and contain from 0.1 to 0.2M of the compound.

The peptide can alternatively be formulated for nasal administration or otherwise administered to the lungs of a subject by any suitable means, e.g., administered by an aerosol suspension of respirable particles comprising the peptide, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the peptide can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the peptide can likewise be produced with any solid particulate medicament aerosol generator, by techniques known in the pharmaceutical art.

Alternatively, one can administer the peptide in a local rather than systemic manner, for example, in a depot or sustained-release formulation.

Further, the present invention provides liposomal formulations of the peptides disclosed herein and salts thereof. The technology for forming liposomal suspensions is well known in the art. When the peptide or salt thereof is an aqueous-soluble salt, using conventional liposome technology, the same can be incorporated into lipid vesicles. In such an instance, due to the water solubility of the peptide or salt, the peptide or salt will be substantially entrained within the hydrophilic center or core of the liposomes. The lipid layer employed can be of any conventional composition and can either contain cholesterol or can be cholesterol-free. When the peptide or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the peptides disclosed herein or salts thereof, can be lyophilized to produce a lyophilizate which can be reconstituted with a pharmaceutically acceptable carrier, such as water, to regenerate a liposomal suspension.

In the case of water-insoluble peptides, a pharmaceutical composition can be prepared containing the water-insoluble peptide, such as for example, in an aqueous base emulsion. In such an instance, the composition will contain a sufficient amount of pharmaceutically acceptable emulsifying agent to emulsify the desired amount of the peptide. Particularly useful emulsifying agents include phosphatidyl cholines and lecithin.

In particular embodiments, the peptide is administered to the subject in a therapeutically effective amount, as that term is defined above. Dosages of pharmaceutically active peptides can be determined by methods known in the art, see, e.g., *Remington's Pharmaceutical Sciences* (Mack Publishing Co., Easton, Pa.). The therapeutically effective dosage of any specific peptide will vary somewhat from peptide to peptide, and patient to patient, and will depend upon the condition of the patient and the route of delivery. As a general proposition, a dosage from about 0.1 to about 50 mg/kg will have therapeutic efficacy, with all weights being calculated based upon the weight of the peptide, including the cases where a salt is employed. Toxicity concerns at the higher level can restrict intravenous dosages to a lower level such as up to about 10 mg/kg, with all weights being calculated based upon the weight of the peptide, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 μmol/kg to 50 μmol/kg, and more particularly to about 22 µmol/kg and to 33 µmol/kg of the peptide for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults.

The present invention is more particularly described in the following examples that are intended as illustrative only since numerous modifications and variations therein will be apparent to those skilled in the art.

EXAMPLE 1

Experimental Methods

Tissue Procurement and Cell Culture: Cells were harvested by enzymatic digestion from human bronchial tissue as previously described under a protocol approved by the UNC School of Medicine IRB (Tarran et al., *J. Gen. Physiol.* 127:591 (2006)). Human excess donor lungs and excised recipient lungs were obtained at the time of lung transplantation from portions of main stem or lumbar bronchi and cells were harvested by enzymatic digestion. All preparations were maintained at an air-liquid interface in a modified bronchial epithelial medium and used 2-5 weeks after seeding on 12 mm T-Clear inserts (Corning Costar) coated with human placental type VI collagen (Sigma). Phosphate buffered saline (PBS) was used for washing human bronchial epithelial culture mucosal surfaces.

Confocal Microscopy: To label airway surface liquid, Ringer containing Texas Red-dextran (2 mg/ml; Invitrogen) was added to human bronchial epithelial culture mucosal surfaces. Perfluorocarbon was added mucosally to prevent evaporation of the airway surface liquid and the culture placed in a chamber containing 100 µl Ringer on the stage of a Leica SP8 confocal microscope with a 63× glycerol immersion objective. 10 points per culture were scanned and an average airway surface liquid height determined. For confocal microscopy human bronchial epithelial cultures were bathed serosally in a modified Ringer solution containing (mM): 116 NaCl, 10 NaHCO$_3$, 5.1 KCl, 1.2 CaCl$_2$, 1.2 MgCl$_2$, 20 TES, 10 glucose, pH 7.4). At all other times, human bronchial epithelial cultures were maintained in a modified BEGM growth medium which contained 24 mM NaHCO$_3$ gassed with 5% CO$_2$. Perfluorocarbon (FC-77) was obtained from 3M and had no effect on ASL height as previously reported.

Internalization of Alpha-ENaC: HEK293T cells were transfected with gfp-αENaC where gfp was fused at the N-terminus of ENaC and unlabeled βENaC and γENaC using lipofectamine in 384 well plates as per the manufacturer's instructions and as published previously (see, e.g., Hobbs et al. Am J Physiol Lung Cell Mol Physiol. 2013 December; 305(12):L990-L1001. doi: 10.1152/ajplung.00103.2013. Epub 2013 October; Garland et al. Proc Natl Acad Sci USA. 2013 Oct. 1; 110(40):15973-8. doi: 10.1073/pnas.1311999110. Epub 2013 Sep. 16.; Tan et al. J Physiol. 2014 Dec. 1; 592(Pt 23):5251-68). Twenty-four hours later, peptide or vehicle control were added at t=0 and fluorescence was read using a Tecan M1000 plate reader 3 h later. Fluorescence was read at 488 and 510 nm.

FIG. 6 shows the results of an experiment analyzing the effects of various peptides on internalization of alpha-ENaC in HEK293T cells when GFP-tagged alpha-ENaC is co-expressed only with gamma ENaC and no beta-ENaC. In this figure, SEQ ID NO:143 (negative control peptide) and water (vehicle) controls are used along with S18 (SEQ ID NO:1, and SEQ ID NO:128. While SEQ ID NO:1 AND SEQ ID NO:128 are effective in reducing alpha-ENaC when beta-ENaC is co-expressed, no effect is observed in this experiment when beta-ENaC is not present.

Efficacy Testing in βENaC Mice: Like CF patients, βENaC-Tg mice are disease free at birth, but soon develop obstructive lung disease (Zhou, Z., et al. Am J Respir Crit Care Med 178, 1245-1256 (2008)). C57BL:FVB and C57BL:C3H mixed strains have 90% and 50% mortality, respectively, and the reproducibility of the disease on these backgrounds is sufficiently high that reliable data are produced with n of about 8-10 animals/group. Furthermore, the βENaC-Tg mouse responds to therapeutic interventions in a fashion similar to CF/COPD in humans, and the development of lung disease can be prevented following inhibition of lung disease at birth (Livraghi, A., et al. J Immunol 182, 4357-4367 (2009)). S18-derived peptides or vehicle were dosed one to three times a day by intranasal instillation (1 µl/g body weight) for 14 days in parallel cohorts of mice. Mice were weighed daily and, if a diuretic effect was found, the volume excreted was replaced by sub-cutaneous injections of sterile saline. At the end of the treatment, mice were sacrificed for phenotypic analysis.

Statistical Analyses: All data are presented as the mean±SE for n experiments. Airway cultures derived from three or more separate donors were used for each study and each oocyte study was repeated on three separate occasions. Differences between means were tested for statistical significance using paired or unpaired t tests or their non parametric equivalent as appropriate to the experiment. From such comparisons, differences yielding P≤0.05 were judged to be significant. All binding assays were fitted to the Hill equation.

EXAMPLE 2

Identification of Specialized Non-naturally Occurring Peptides

Based on the ability of normal human bronchial epithelial cultures to regulate airway surface liquid height to 7 µm, which was paralleled by a decrease in trypsin-sensitive ENaC activity, we previously demonstrated that SPLUNC1 derived peptides (namely, S18; FIG. 1) can inhibit ENaC with EC$_{50}$ in the sub micromolar range for up to 24 h following a single dose (Hobbs et al., 2013). While S18 is resistant to proteolysis and heat-stable, we tested whether we could reduce the size of S18, increase its stability and/or increase its potency. Any of these actions would increase its utility as a drug.

Figures 2A, 2B:
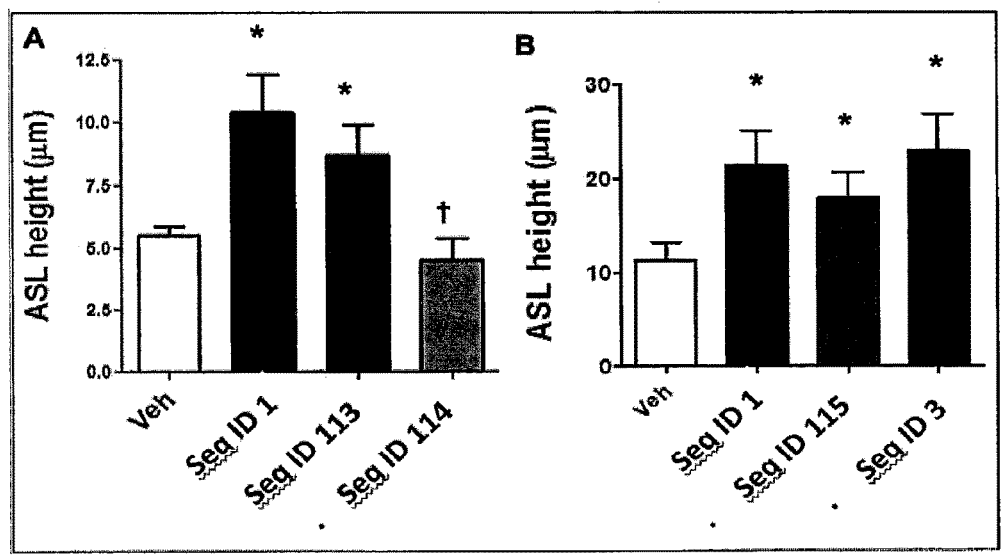
FIGS. 2A-2B show the 1$^{st}$ half (LPVPLDQT (SEQ ID NO:113) but not the remainder (DQTLPLNVNP (SEQ ID NO:114) of S18 is required for inhibition of ENaC and preservation of ASL height.

To confirm our alanine-scan data, we made a peptide of subsequence A (LPVPLDQT (SEQ ID NO:113); FIG. 1). As a control, we made an overlapping 2nd peptide, which contained the charged mid-region (DQT), as well as subsequence B (DQTLPLNVNP (SEQ ID NO:114)). As shown in FIG. 2, LPVPLDQT (SEQ ID NO:113) retained similar activity to S18, whilst DQTLPLNVNP (SEQ ID NO:114)

was inactive. However, additional experiments, where we examined susceptibility to proteases, demonstrated that whilst LPVPLDQT (SEQ ID NO:113) could inhibit ENaC-led fluid absorption, this peptide was more susceptible to proteolytic degradation. Thus, we generated new peptides where we flanked the C- and N-termini with a pair of D-alanines (shown as lower case 'a'). Peptides were added mucosally to HBECs at 30 μM and ASL height measured 3 h later by XZ-confocal microscopy. FIG. 2A shows the comparison of the N-terminal region of S18 (LPVPLDQT) (SEQ ID NO:113) vs. an overlapping, but C-terminal segment (DQTLPLNVNP) (SEQ ID NO:114). In FIG. 2B, D-alanines were added to Sub-S18 peptides LPVPLDQT (SEQ ID NO:113) and LPVPLDQTLPL (SEQ ID NO:115) to increase the stability of LPVPLDQT (SEQ ID NO:113). D-alanines are noted as lowercase a. All n=6-9. Data are shown as mean±SEM.

Figures 3A, 3B:
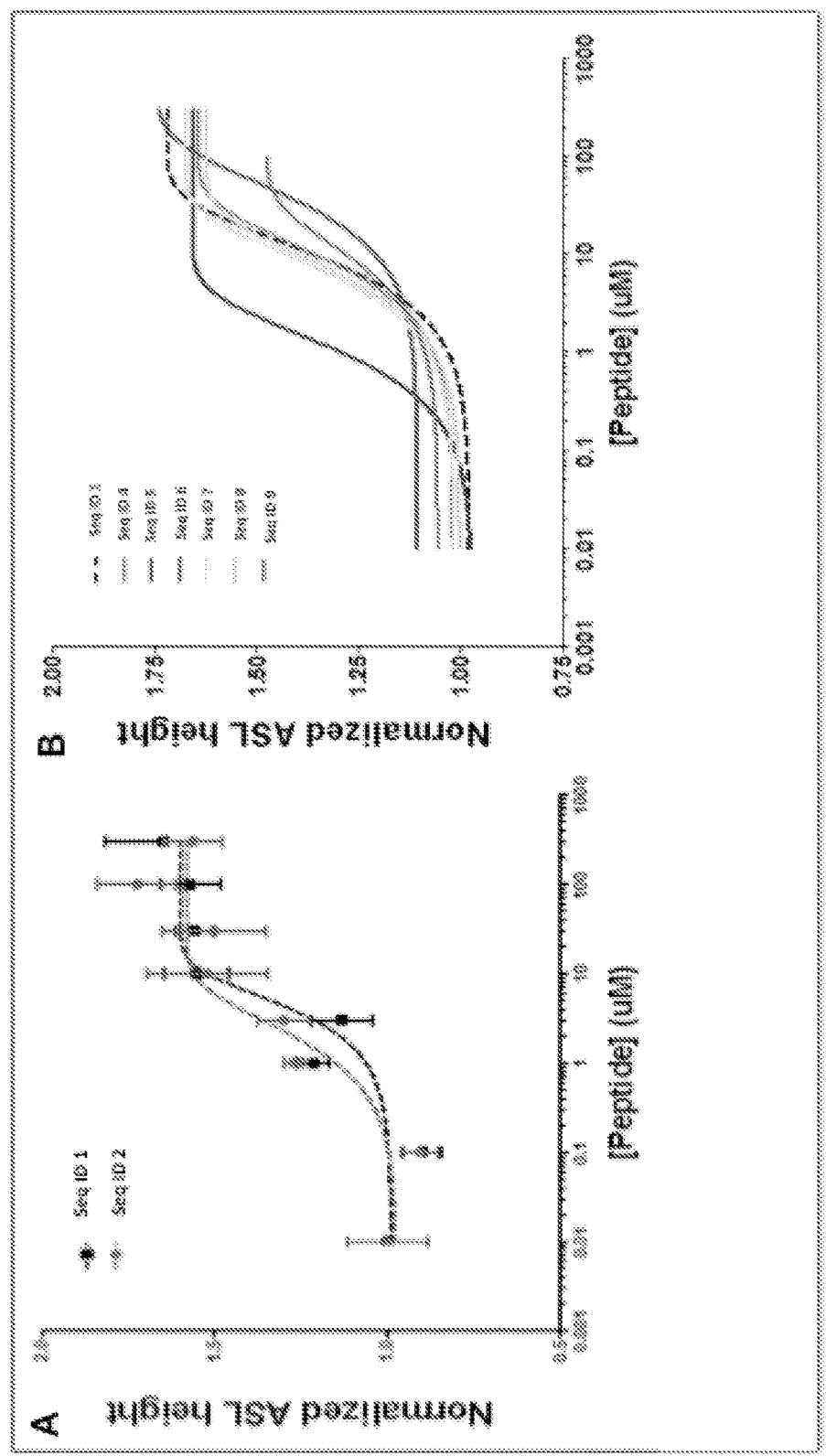
FIG. 3A shows that S18 (SEQ ID NO:1) and aaLPV-PLDQTLPLNVNPaa (SEQ ID NO:2) have equal potency and efficacy, despite SEQ ID NO:2 being flanked by D-alanines.
FIG. 3B shows that S18, and aaLPVPLDQTaa (SEQ ID NO:3) have equal potency and efficacy, despite (SEQ ID NO:3) being flanked by D-alanines FIG. 3A also shows the relative potency of a sample of peptides, including aaLPN-lePLDQTaa (SEQ ID NO:5), which displays increased potency, relative to S18 or SEQ ID NO:4.

The 15-mer and 8-mer showed identical activity when compared against S18 (FIGS. 2A-2B). We then generated full dose-responses for S18 vs. the peptide aaLPVPLDQTaa (SEQ ID NO:3). S18 and aaLPVPLDQTaa (SEQ ID NO:3) produced identical dose responses (FIG. 3A), indicating that shortening the peptide and flanking it with unnatural amino acids did not affect its potency or efficacy. Next, we made several new peptides based on the sequence of SEQ ID NO:2. Here, since prolines typically provide kinks in a peptide, they were not altered and instead, we systematically made conservative substitutions of the other amino acids. The dose responses are shown in FIG. 3B. Note, since there are several lines on this graph, the error bars and data symbols were omitted. However, these data were obtained simultaneously using paired airway cultures, so their comparison is valid. Clearly, SEQ ID NO:5 (aaLPNlePLDQTaa) shows a log-fold increase in potency as compared to S18, whilst SEQ ID NO:9 (aaLPVPLDQSaa) and SEQ ID NO:6 (aaLPVPNleDQTaa) show diminished potency and efficacy respectively (FIG. 3B). Other sequences included in FIG. 3B are SEQ ID NO:4 (aaNlePVPLDQTaa), SEQ ID NO:7 (aaLPVPLDNTaa) and SEQ ID NO:8 (aaLPVPLEQTaa).

Figure 4:
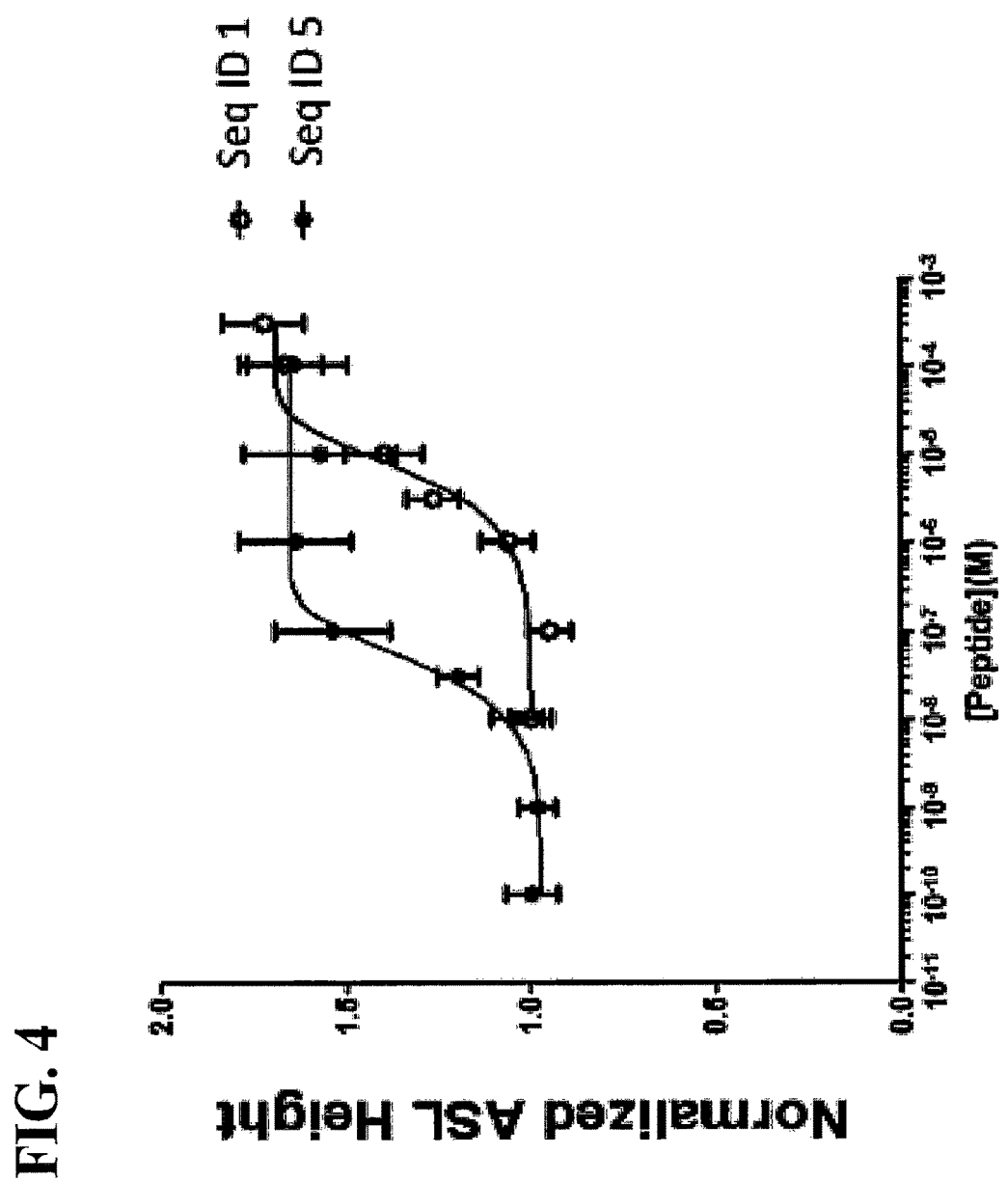
FIG. 4 shows an additional comparison of S18 and SEQ ID NO:5, and increased potency of SEQ ID NO:5.

Using a fresh batch of airway cells, we performed an additional dose response to SEQ ID NO:5 (FIG. 4). As can be seen, this peptide gave a significant increase in potency, as compared to S18, and the $IC_{50}$ was 30 nM.

Figure 5A:
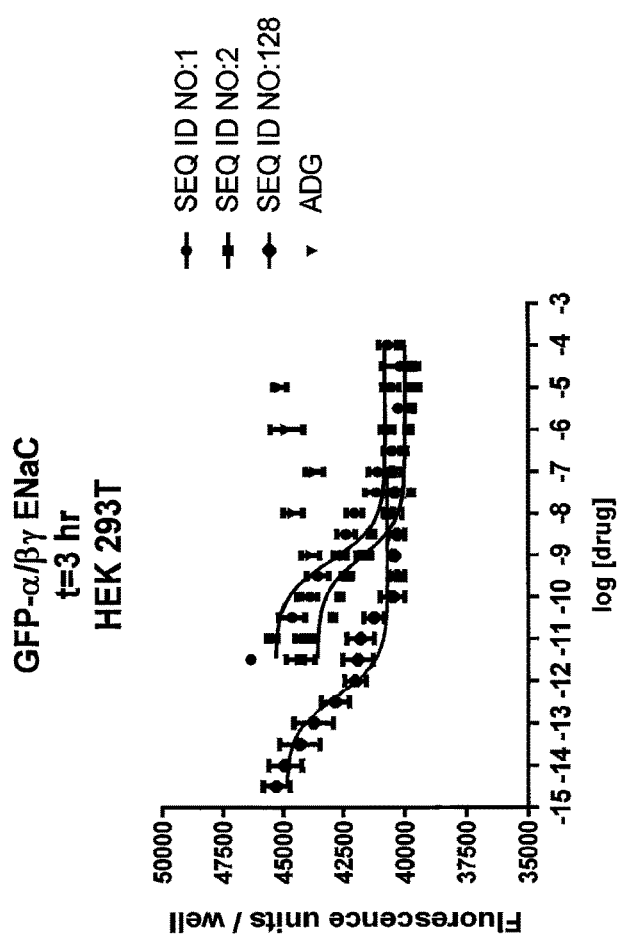
FIGS. 5A-5U show the results of experiments analyzing the effects of various peptides on internalization of alpha-ENaC in HEK293T cells and effects on cell viability when GFP-tagged alpha-ENaC is co-expressed with beta and gamma ENaC. EC50 values are shown at the bottom of several of the figures. In these figures, ADG is a negative control peptide with the sequence: NH3-ADGGLLLLN-NPPPPQTVV-NH2 (SEQ ID NO:143). The peptides used in these experiments were S18 (SEQ ID NO:1), SEQ ID NO:2, SEQ ID NO:141, SEQ ID NO:129, SEQ ID NO:130, SEQ ID NO:128, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:131, SEQ ID NO:139; SEQ ID NO:140, SEQ ID NO:144 and SEQ ID NO:127. Also used in these experiments were peptides of SEQ ID NO:12, SEQ ID NO:13, SEQ ID NO:16, SEQ ID NO:17, SEQ ID NO:18, and SEQ ID NO:136, each with an aa cap at both the N- and the C-terminus. Also shown is amiloride, which inhibits ENaC by another mechanism and does not reduce the amount of functional receptor on the surface of cells.
Figure 5B:
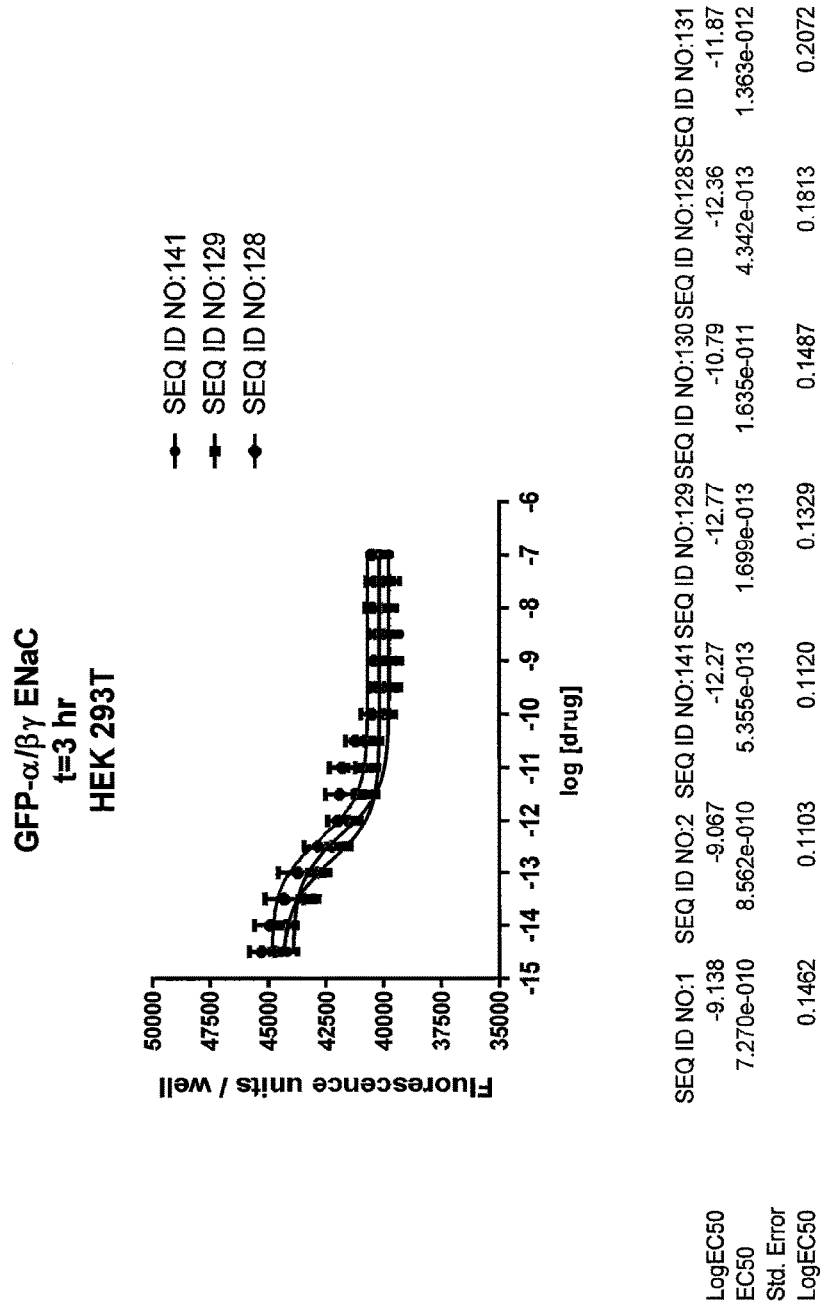
Figure 5C:
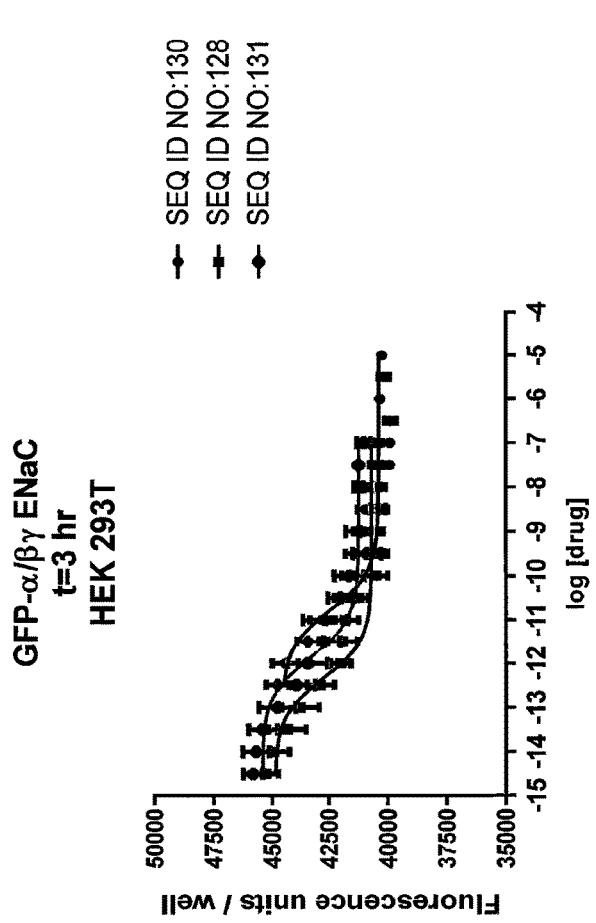
Figure 5D:
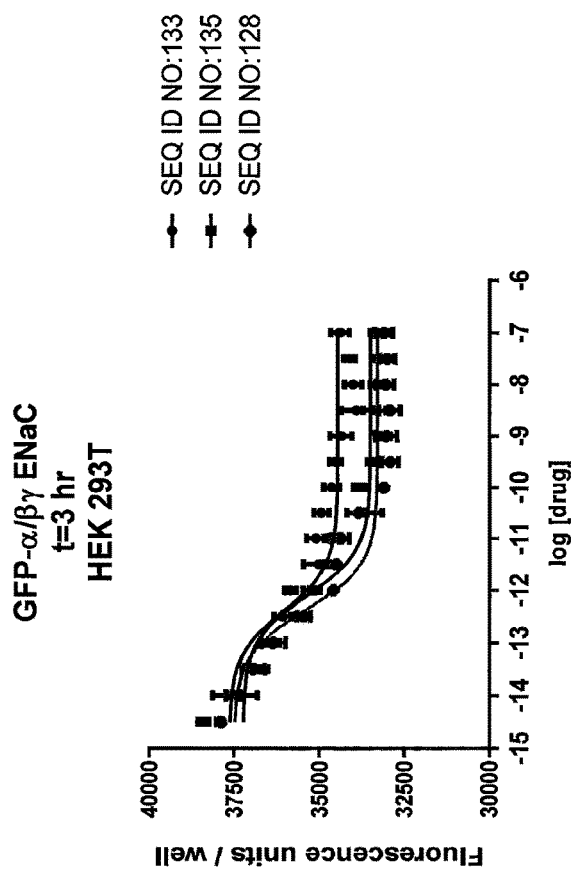
Figure 5F:
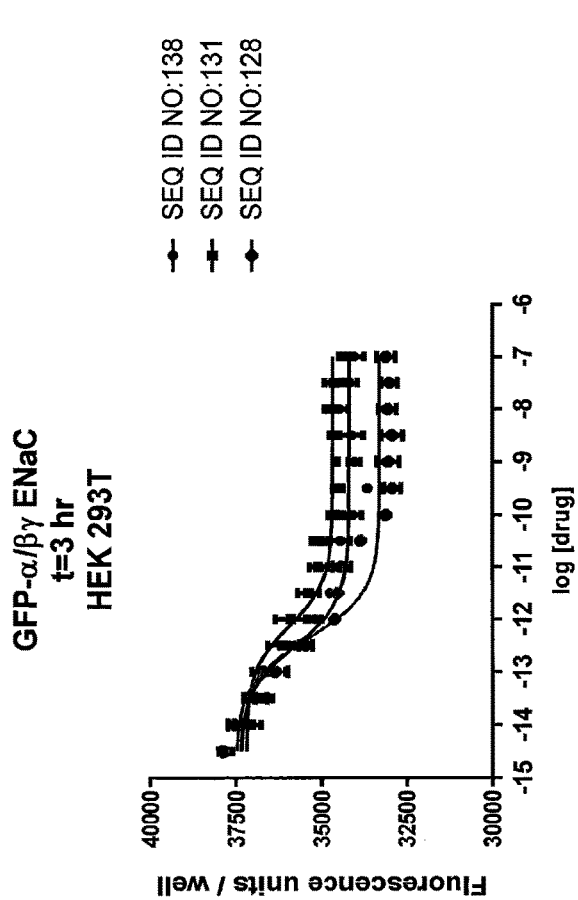
Figure 5G:
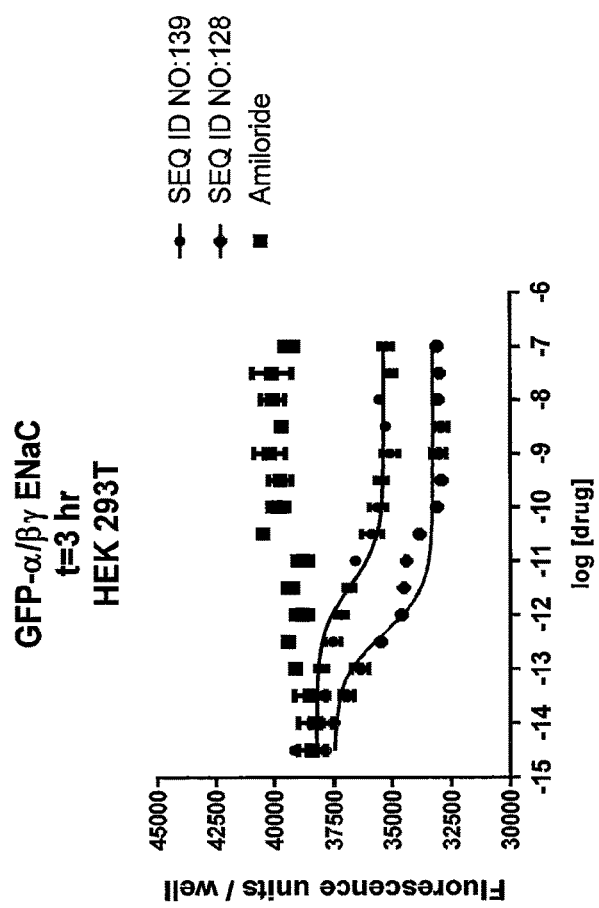
Figure 5H:
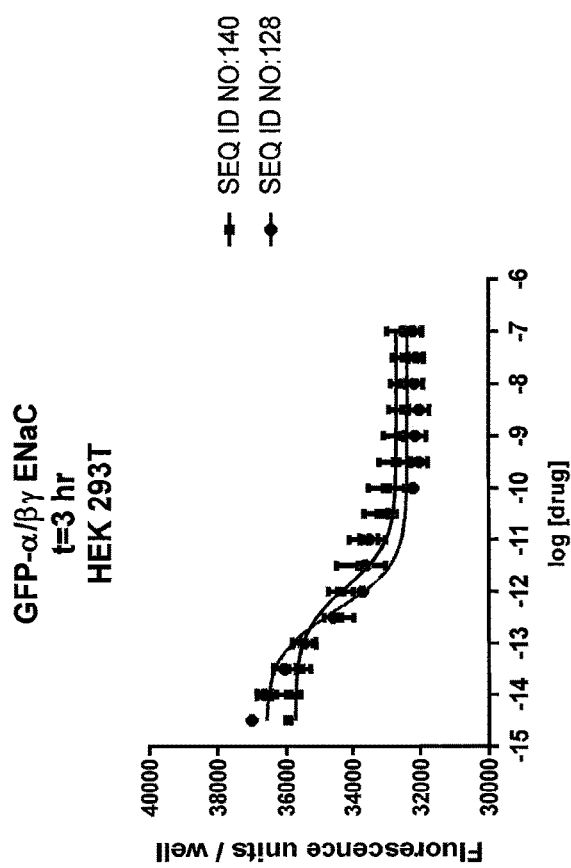
Figure 51:
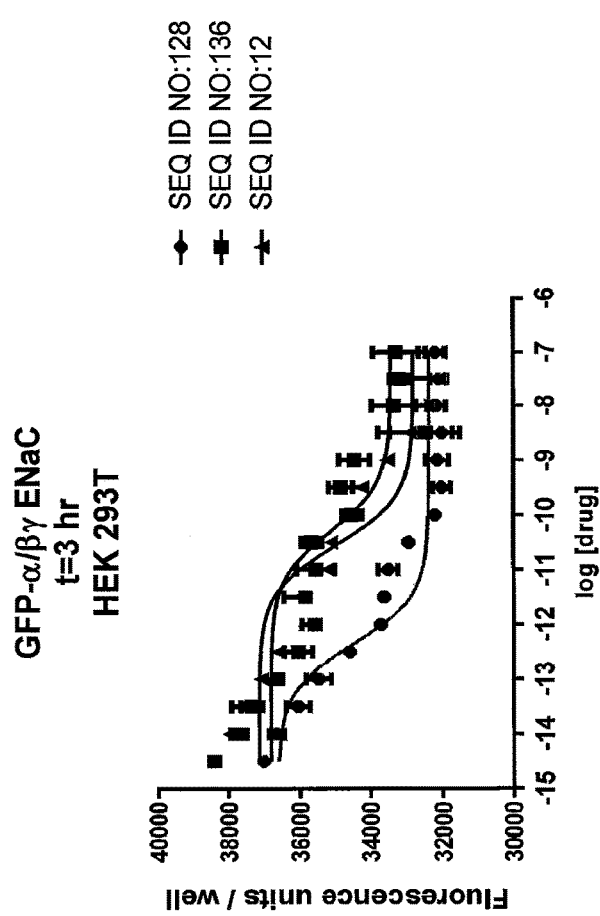
Figure 5J:
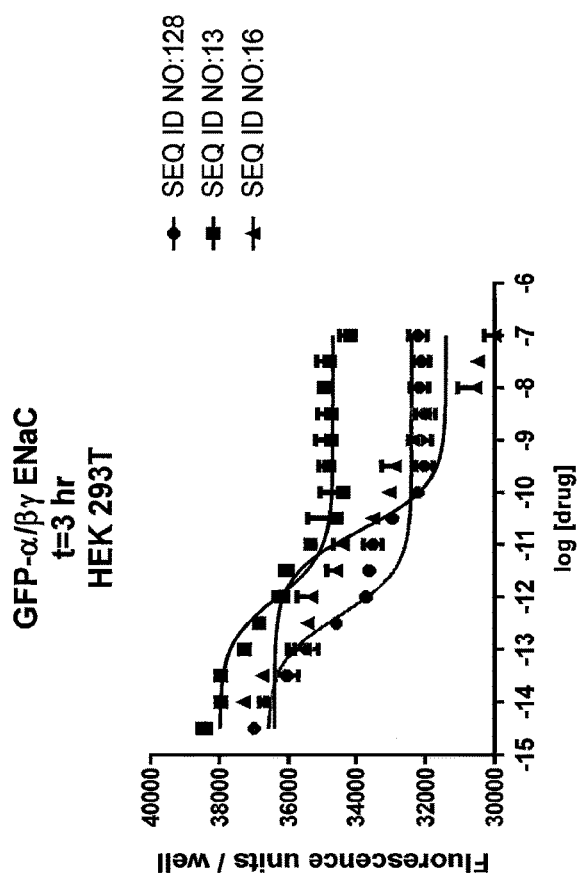
Figure 5K:
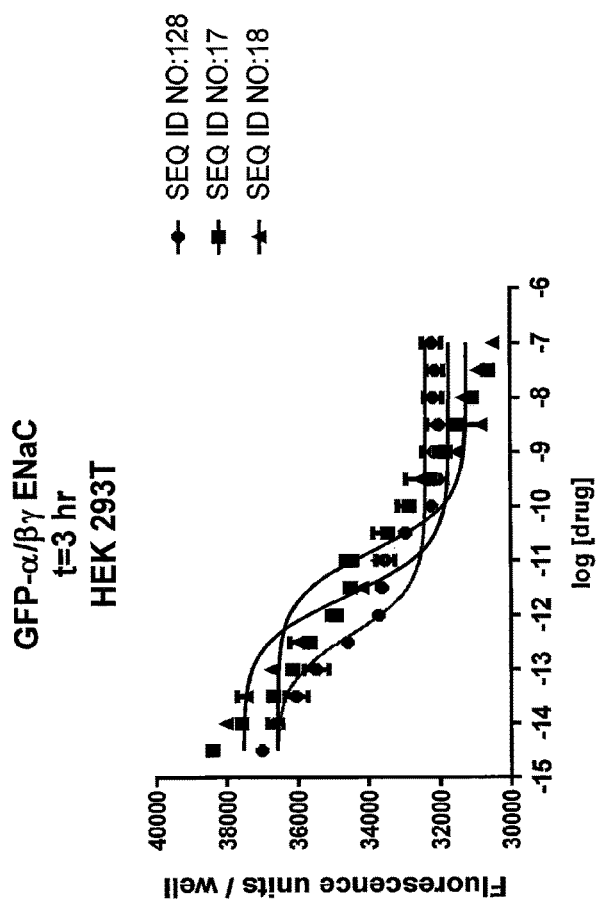
Figure 5L:
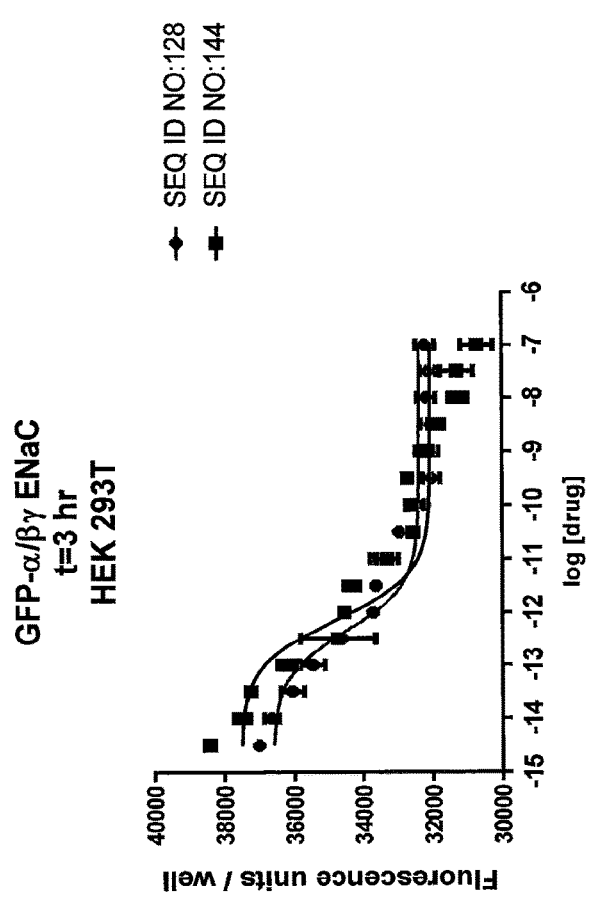
Figure 5M:
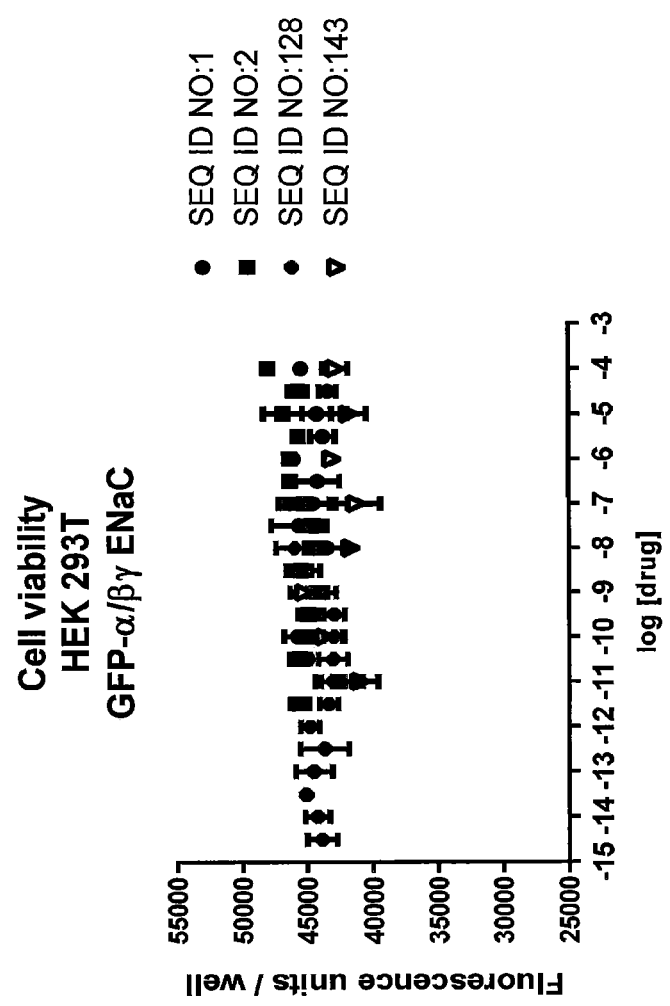
Figure 5N:
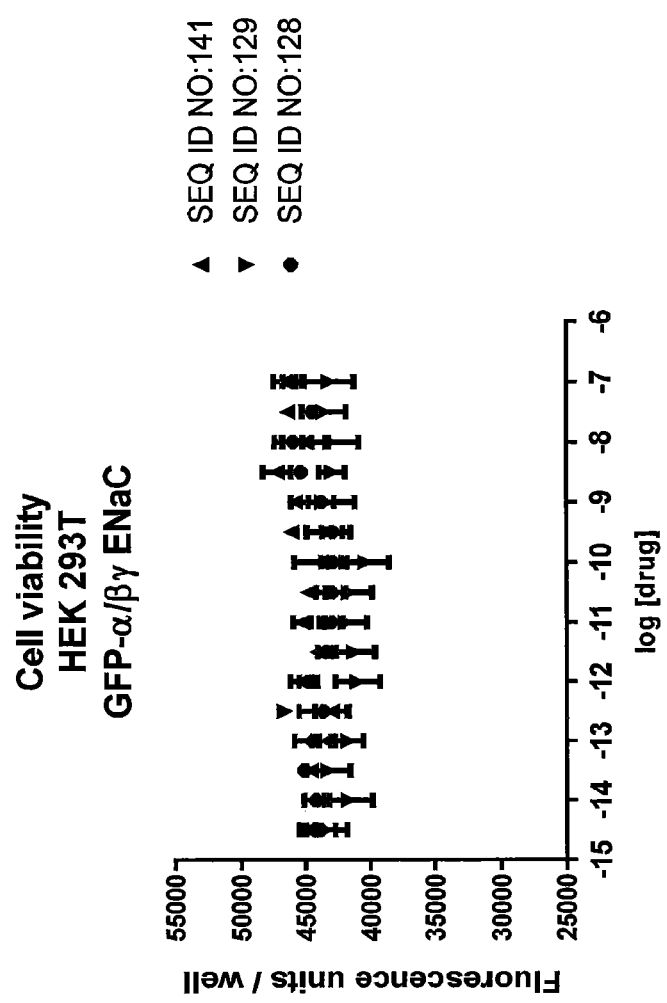
Figure 50:
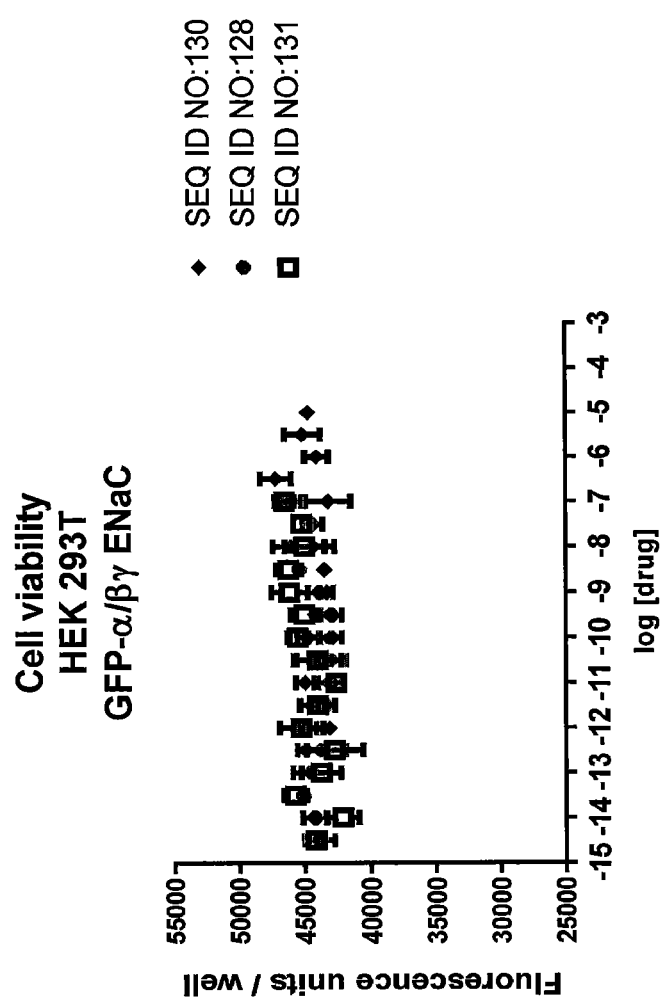
Figure 5P:
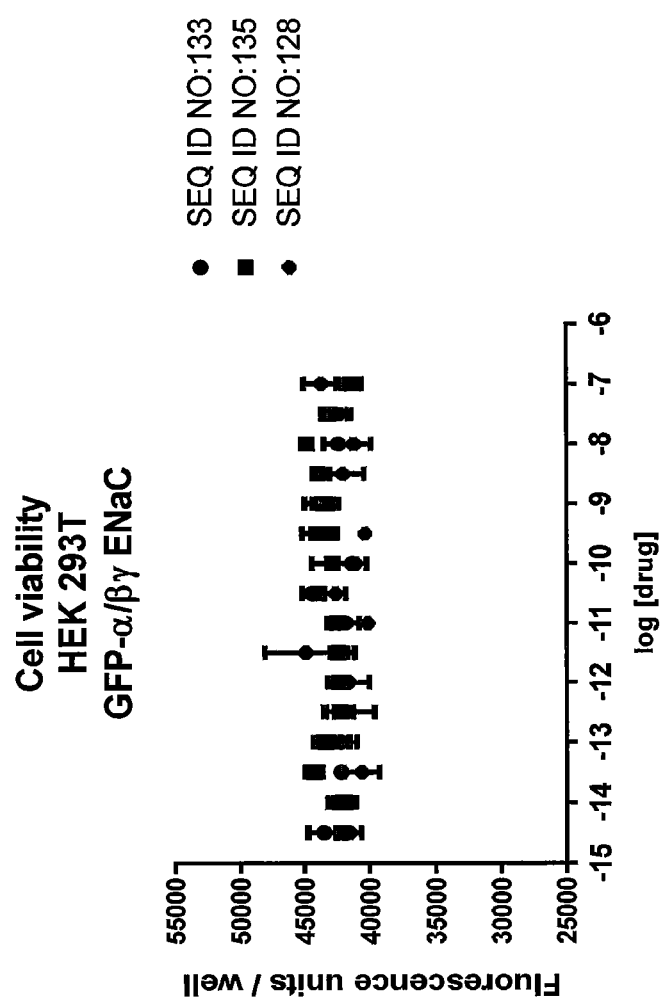
Figure 5Q:
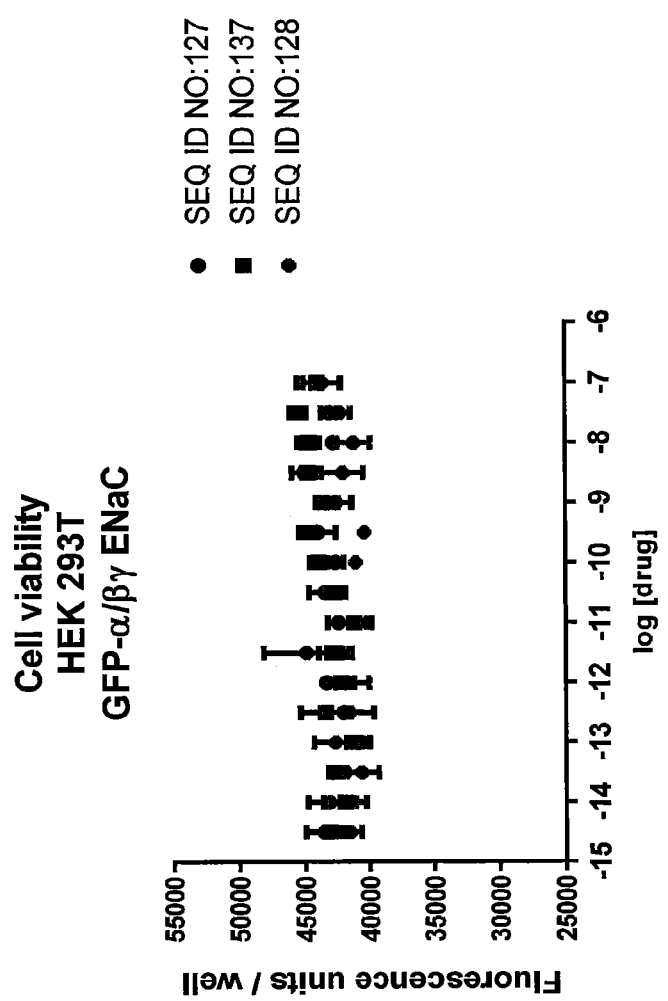
Figure 5R:
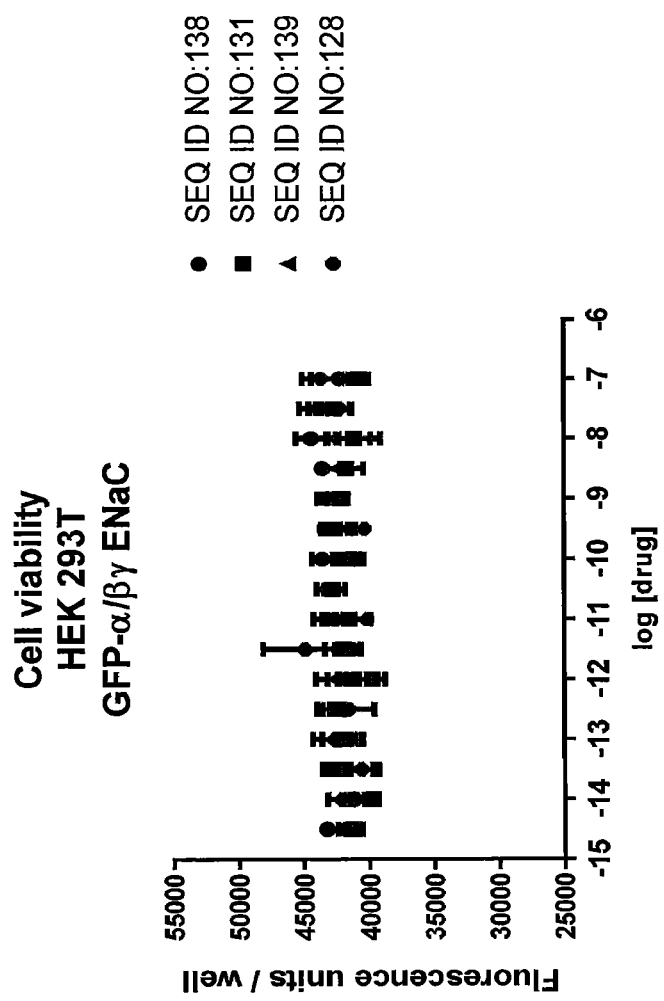
Figure 5S:
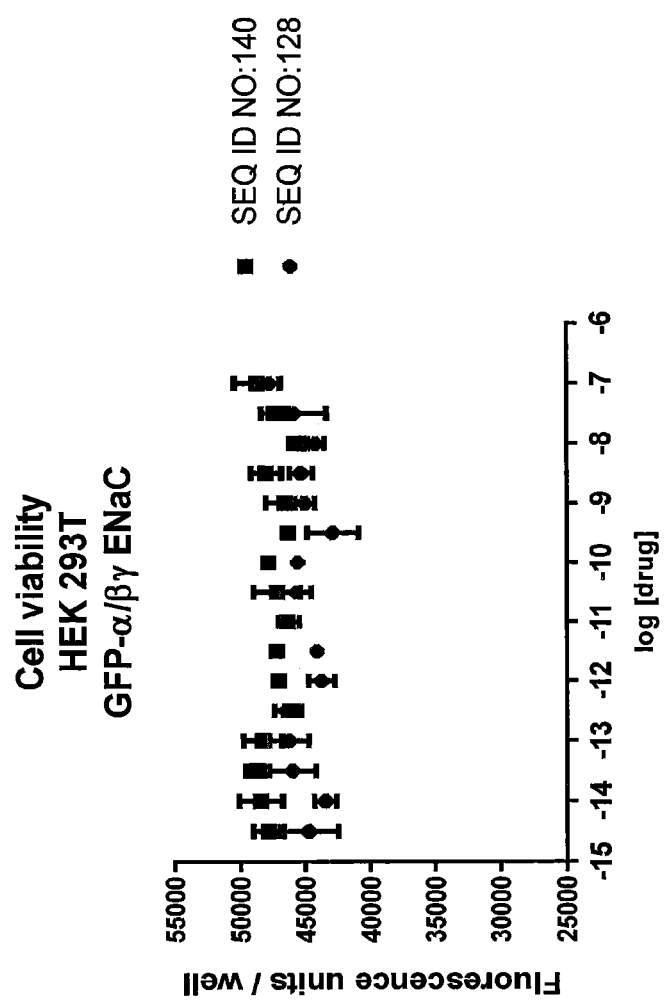
Figure 5T:
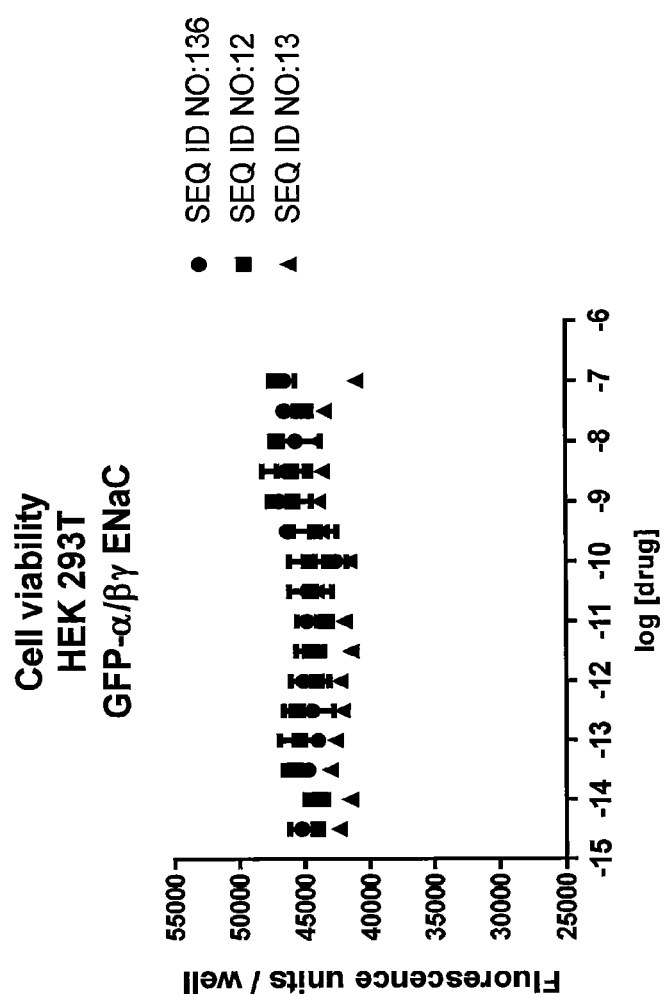
Figure 5U:
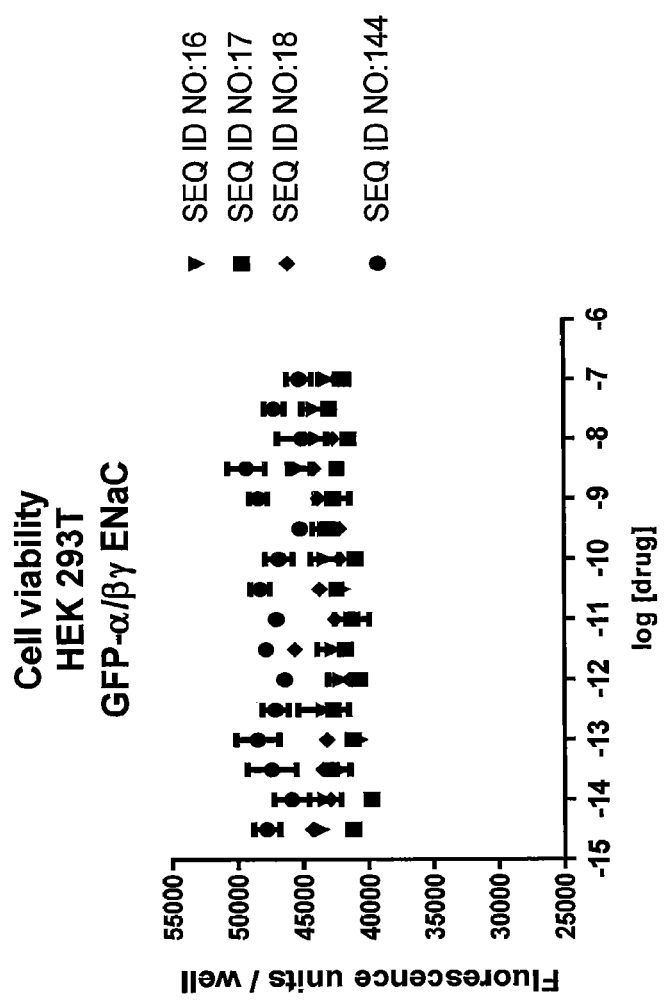

The ability of the peptides to modulate internalization of αENaC was tested. Results from these experiments are shown in FIGS. 5A-5U. ADG is a negative control peptide with the sequence: NH3-ADGGLLLLNNPPPPQTVV-NH2 (SEQ ID NO:143). The peptides used in these experiments were S18 (SEQ ID NO:1), SEQ ID NO:2, SEQ ID NO:141, SEQ ID NO:129, SEQ ID NO:130, SEQ ID NO:128, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:131, SEQ ID NO:139; SEQ ID NO:140, SEQ ID NO:144 and SEQ ID NO:127. Also used in these experiments were peptides of SEQ ID NO:12, SEQ ID NO:13, SEQ ID NO:16, SEQ ID NO:17, SEQ ID NO:18, and SEQ ID NO:136, each with an aa cap at both the N- and the C-terminus. Also shown is amiloride, which inhibits ENaC by another mechanism and does not reduce the amount of functional receptor on the surface of cells. These results demonstrate that the SPLUNC peptides trigger the destruction of the ENaC function to inhibit its activity.

Figure 7A:
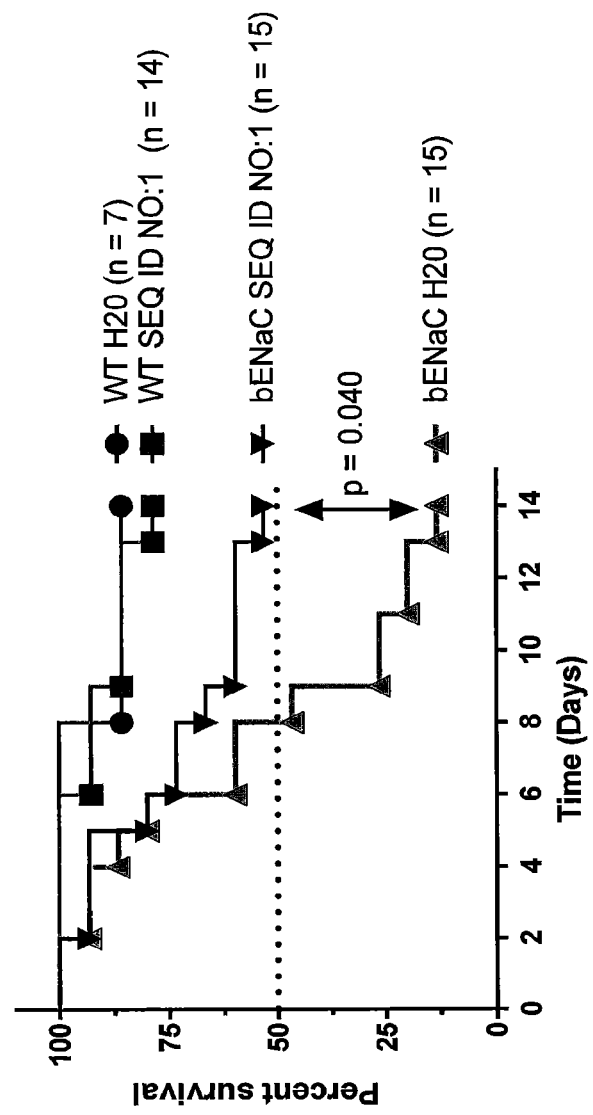
FIG. 7A shows the results of an experiment analyzing the effect on percent survival of βENaC-Tg C57BL:FVB mice after treatment with the S18 peptide (SEQ ID NO:1). S18 (100 mM solution) was administered 3 times per day at 1 µL/g of body weight.
Figure 7B:
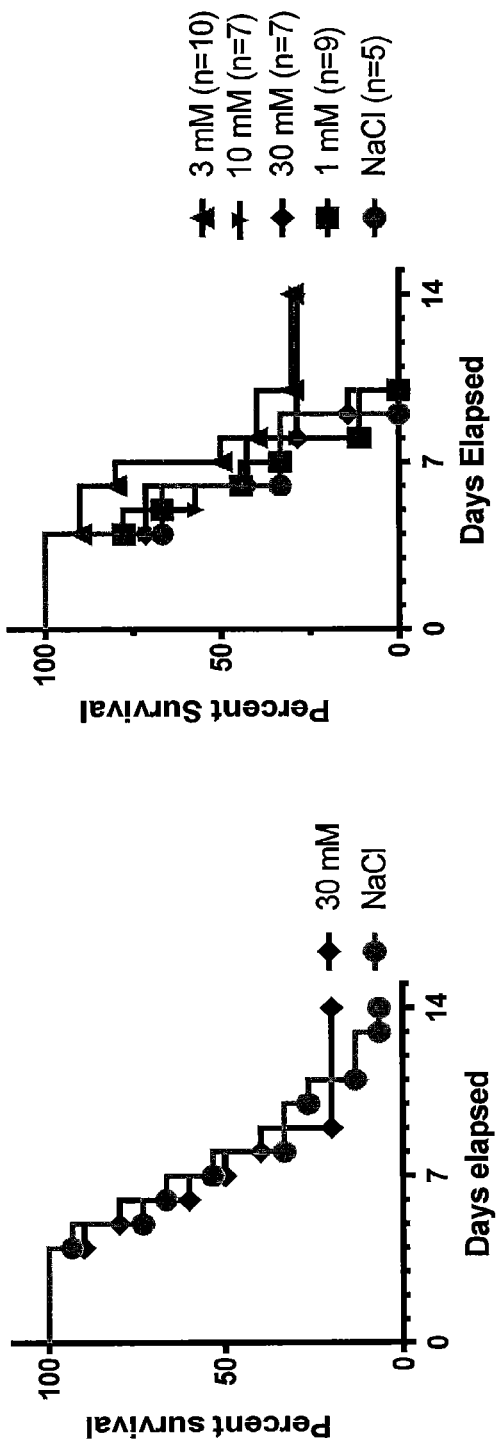
FIG. 7B shows the results of an experiment analyzing the effect on percent survival of βENaC-Tg C57BL:FVB mice after treatment with inhaled SEQ ID NO:142 or SEQ ID NO:128.
Figure 7C:
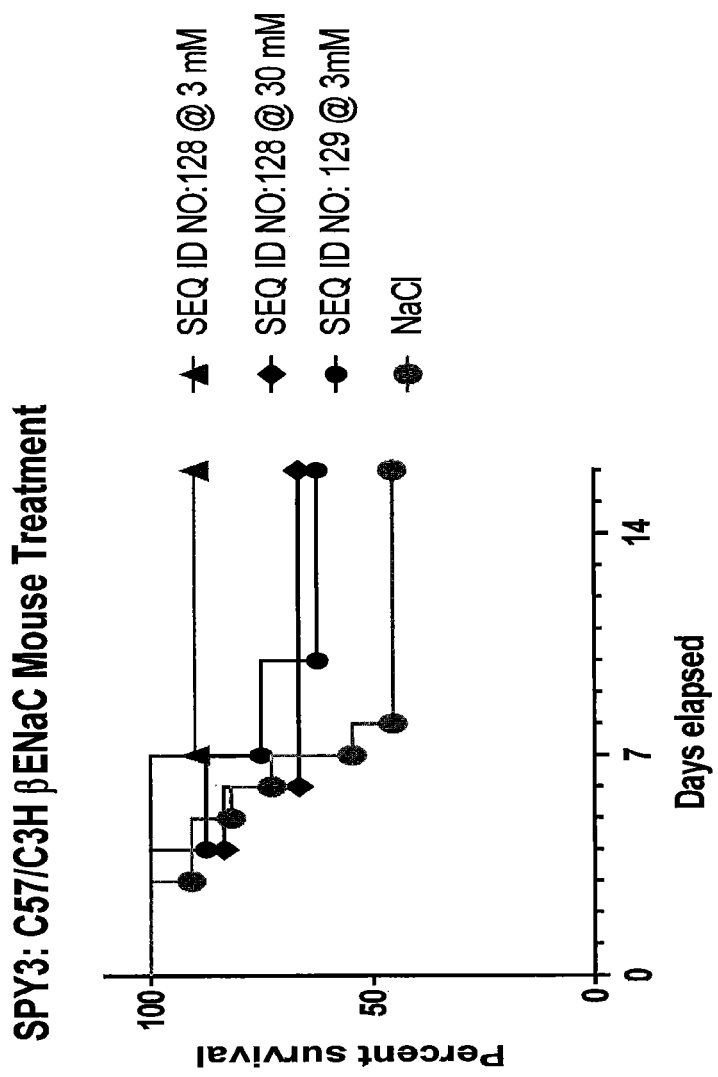
FIGS. 7C and 7D show the results of an experiment analyzing the effect on percent survival of βENaC-Tg C57BL:C3H mice after treatment with SEQ ID NO:129 or SEQ ID NO:128.
Figure 7D:
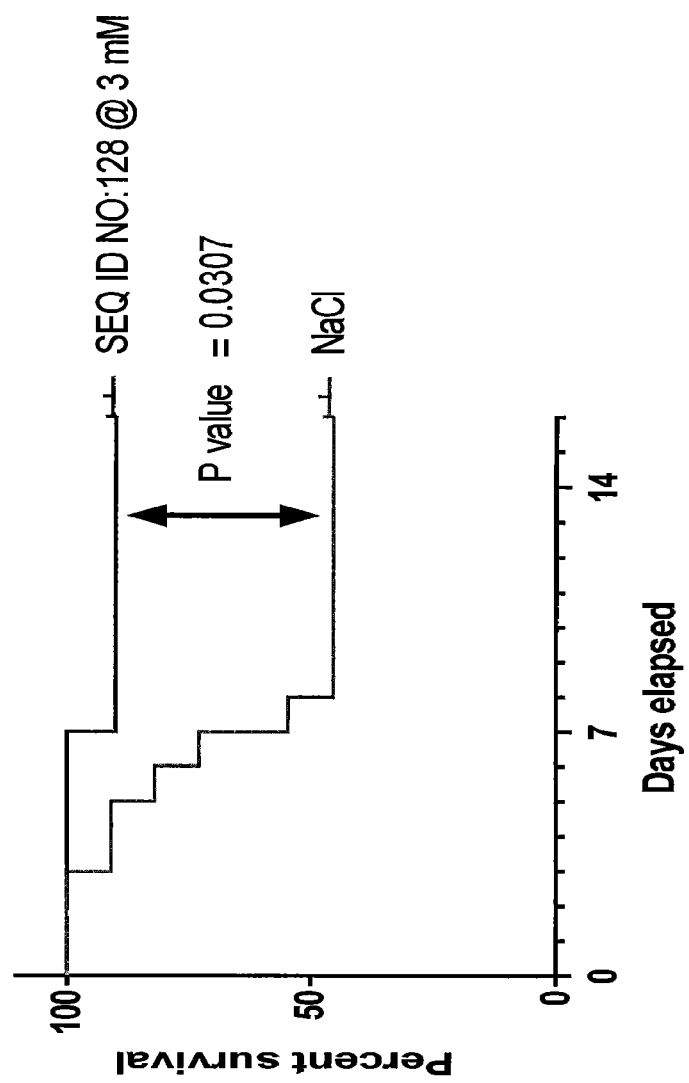
Figure 7E:
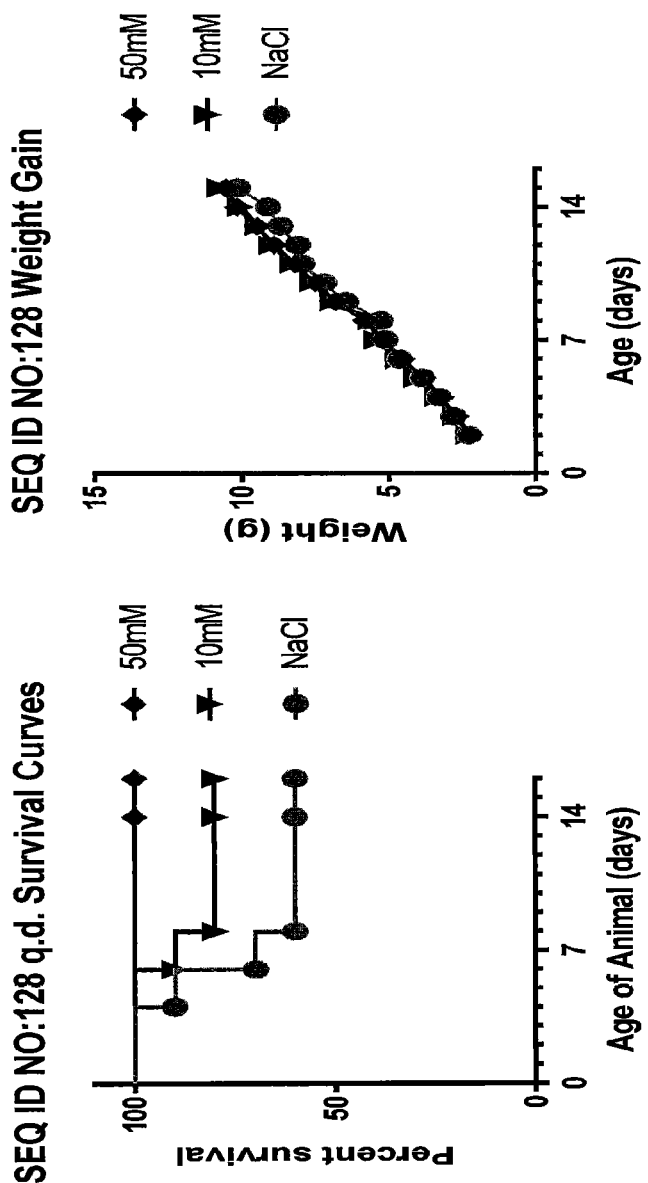
FIG. 7E show the results of an experiment analyzing the effect on percent survival (left panel) and weight gain (right panel) of βENaC-Tg C57BL:C3H mice after treatment with a once daily dose of SEQ ID NO:128.
Figure 7F:
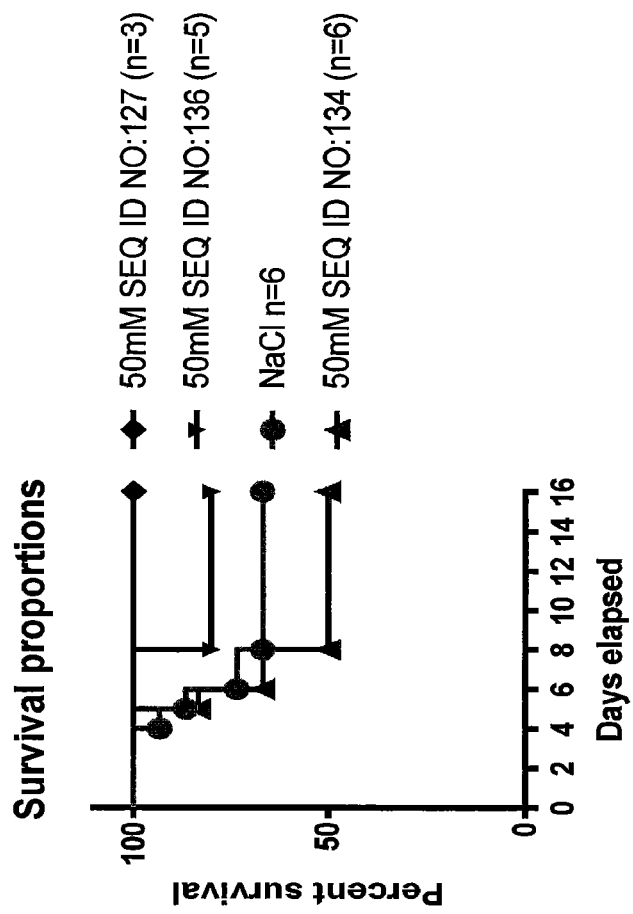
FIG. 7F shows the results of an experiment analyzing the effect on percent survival of βENaC-Tg C57BL:C3H mice after treatment with SEQ ID NO:127, SEQ ID NO:134, or SEQ ID NO:136.

The efficacy of the peptides was tested in βENaC mice. Results from these experiments are shown in FIGS. 7A-7F. Fourteen-day treatment with inhaled SEQ ID NO:128 was more effective than inhaled SEQ ID NO:142 at increasing percent survival of βENaC-Tg C57BL:FVB mice (FIG. 7B). Fourteen-day treatment with SEQ ID NO:128 also increased percent survival of βENaC-Tg C57BL:C3H mice (FIGS. 7C and 7D). Once daily dosing with SEQ ID NO:128 increased percent survival of βENaC-Tg C57BL:C3H mice (FIG. 7E, left panel). The right panel of FIG. 7E shows that SEQ ID NO:128 did not have a diuretic effect. FIG. 7F shows that treatment with SEQ ID NO:127 increased percent survival of ENaC-Tg C57BL:C3H mice. Sequences of other peptides used in the experiment were SEQ ID NO:129, SEQ ID NO:134, and SEQ ID NO:136.

The foregoing is illustrative of the present invention, and is not to be construed as limiting thereof. The invention is defined by the following claims, with equivalents of the claims to be included therein.

That which is claimed is:

1. A method of treating a lung disorder comprising administering to a subject in need thereof an effective amount of a fusion polypeptide and saline, wherein the fusion polypeptide comprises an epithelial sodium channel (ENaC) internalization-inducing peptide and a heterologous peptide, wherein the ENaC internalization-inducing peptide is SEQ ID NO:127, wherein the lung disorder is selected from the group consisting of cystic fibrosis, non-cystic fibrosis bronchiectasis, chronic obstructive pulmonary disease, acute bronchitis, chronic bronchitis and asthma.

2. The method of claim 1, wherein a heterologous peptide is fused to the amino terminus of the ENaC internalization-inducing peptide or to the carboxy terminus of the ENaC internalization-inducing peptide.

3. The method of claim 1, wherein a first heterologous peptide is fused to the amino terminus of the ENaC internalization-inducing peptide and a second heterologous peptide is fused to the carboxy terminus of the ENaC internalization-inducing peptide.

4. The method of claim 3, wherein the first heterologous peptide and the second heterologous peptide are the same.

5. The method of claim 1, wherein the heterologous peptide comprises one or more non-naturally occurring amino acids.

6. The method of claim 1, wherein the heterologous peptide consists of one or more non-naturally occurring amino acids.

7. The method of claim 1, wherein the heterologous peptide consists of two non-naturally occurring amino acids.

8. The method of claim 1, wherein the heterologous peptide consists of D-Ala-D-Ala.

9. The method of claim 1, wherein the fusion polypeptide consists of SEQ ID NO:128.

10. The method of claim 1, wherein the fusion polypeptide induces cellular internalization of ENaC.

11. The method of claim 1, wherein the fusion polypeptide induces cellular internalization of ENaC by HEK293T cells that express human alpha-, beta-, and gamma-ENaC.

12. The method of claim 1, wherein the fusion polypeptide and the saline are administered to the lung of the subject in need thereof.

13. The method of claim 1, wherein the saline comprises normal saline.

14. The method of claim 1, wherein the saline comprises hypertonic saline.

15. The method of claim 9, wherein the lung disorder is cystic fibrosis.

16. The method of claim 9, wherein the saline comprises normal saline.

17. The method of claim 9, wherein the saline comprises hypertonic saline.

18. The method of claim 9, wherein the lung disorder is cystic fibrosis.

* * * * *